US012802786B2

(12) United States Patent
Yokoyama et al.

(10) Patent No.: US 12,802,786 B2
(45) Date of Patent: Nov. 17, 2026

(54) INFORMATION PROCESSING METHOD, INFORMATION PROCESSING SYSTEM, AND RECORDING MEDIUM

(71) Applicant: Panasonic Intellectual Property Management Co., Ltd., Osaka (JP)

(72) Inventors: Tomoyasu Yokoyama, Osaka (JP); Kazuhide Ichikawa, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 126 days.

(21) Appl. No.: 18/888,234

(22) Filed: Sep. 18, 2024

(65) Prior Publication Data

US 2025/0014273 A1 Jan. 9, 2025

Related U.S. Application Data

(63) Continuation of application No. PCT/JP2023/001943, filed on Jan. 23, 2023.

(30) Foreign Application Priority Data

Mar. 31, 2022 (JP) ................................ 2022-057910

(51) Int. Cl.
*G16C 60/00* (2019.01)
*G06F 3/14* (2006.01)
(Continued)

(52) U.S. Cl.
CPC .............. *G16C 60/00* (2019.02); *G06T 19/20* (2013.01); *G16C 20/10* (2019.02); *G16C 20/20* (2019.02);
(Continued)

(58) Field of Classification Search
CPC ......... G06T 17/20; G06T 19/20; G06T 17/00; G06T 2219/2004; G06T 2219/2016;
(Continued)

(56) References Cited

U.S. PATENT DOCUMENTS 5,448,687 A * 9/1995 Hoogerhyde ........... G06T 19/00 345/423
6,441,814 B1 * 8/2002 Mine ....................... G06T 17/00 345/419
(Continued)

FOREIGN PATENT DOCUMENTS

JP H06250999 A * 9/1994 ............. G06T 17/20
JP 2009042616 A * 2/2009
(Continued)

OTHER PUBLICATIONS

International Search Report of PCT application No. PCT/JP2023/001943 dated Mar. 14, 2023.
(Continued)

*Primary Examiner* — Michael J Jansen, II
(74) *Attorney, Agent, or Firm* — Wenderoth, Lind & Ponack, L.L.P.

(57) ABSTRACT

An information processing method is an information processing method executed by a computer, and includes acquiring first information concerning polyhedra; generating second information concerning a three-dimensional structure in which the polyhedra are arranged on the basis of the first information; and outputting the second information thus generated. The three-dimensional structure is a structure in which the polyhedra are arranged without any gaps and becomes a crystal structure in a case where atoms are arranged.

16 Claims, 37 Drawing Sheets

(51) Int. Cl.

| | |
|---|---|
| ***G06F 30/10*** | (2020.01) |
| ***G06F 30/20*** | (2020.01) |
| ***G06T 17/00*** | (2006.01) |
| ***G06T 17/20*** | (2006.01) |
| ***G06T 19/20*** | (2011.01) |
| ***G16C 20/10*** | (2019.01) |
| ***G16C 20/20*** | (2019.01) |
| ***G16C 20/40*** | (2019.01) |
| ***G16C 20/80*** | (2019.01) |

(52) U.S. Cl.
CPC ............ *G16C 20/40* (2019.02); *G16C 20/80* (2019.02); *G06F 3/14* (2013.01); *G06F 30/10* (2020.01); *G06F 30/20* (2020.01); *G06T 17/00* (2013.01); *G06T 17/20* (2013.01); *G06T 2219/2004* (2013.01); *G06T 2219/2016* (2013.01); *G06T 2219/2021* (2013.01)

(58) Field of Classification Search
CPC ... G06T 2219/2021; G06F 3/14; G06F 30/10; G06F 30/20; G16C 60/00; G16C 20/10; G16C 20/20; G16C 20/40; G16C 20/80
See application file for complete search history.

(56) References Cited

U.S. PATENT DOCUMENTS

| | | | | |
|---|---|---|---|---|
| 12,296,537 | B2 * | 5/2025 | Waldvogel | B29C 64/386 |
| 2012/0150512 | A1 * | 6/2012 | Takai | G16C 10/00 703/2 |
| 2018/0186070 | A1 | 7/2018 | Yun et al. | |
| 2022/0203621 | A1 * | 6/2022 | Waldvogel | B29C 64/386 |
| 2023/0290063 | A1 * | 9/2023 | Mammou | G06T 17/20 |
| 2024/0013852 | A1 * | 1/2024 | Gang | B82Y 30/00 |
| 2024/0127121 | A1 * | 4/2024 | Shinagawa | G06N 3/042 |
| 2024/0144045 | A1 * | 5/2024 | Amii | G16C 60/00 |
| 2024/0144046 | A1 * | 5/2024 | Amii | G16C 20/70 |
| 2025/0006314 | A1 * | 1/2025 | Yokoyama | G16C 20/30 |
| 2025/0014273 | A1 * | 1/2025 | Yokoyama | G06F 3/14 |
| 2025/0028869 | A1 * | 1/2025 | Yokoyama | G06F 30/13 |
| 2025/0029683 | A1 * | 1/2025 | Ueno | G16C 20/20 |

FOREIGN PATENT DOCUMENTS

| | | | | |
|---|---|---|---|---|
| JP | 2010198684 A | * | 9/2010 | B41J 3/4071 |
| JP | 2018-516794 | | 6/2018 | |

OTHER PUBLICATIONS

Kengo Nishio et al., “How to describe disordered structures”, Scientific Reports, 6, Apr. 11, 2016, 23455.

CrystalMaker: Overview, [online], Jan. 22, 2022, pp. 1-15. URL:https://web.archive.org/web/20220122203156/http:/crystalmaker.com/crystalmaker/index.html.

Screen captures from YouTube video clip entitled “Building a New Crystal” play time 0:20-0:28, uploaded on Jul. 31, 2018 by user “CrystalMaker Software” Date Accessed: Jul. 22, 2024. Retrieved from Internet: <https://www.youtube.com/watch?v=AnYD0ERAfJw&pp=ugMICgJqYRABGAE%3D>.

CrystalViewer: Introduction, [online], Dec. 29, 2021, pp. 1-11. URL:https://web.archive.org/web/20211229165639/http:/crystalmaker.com/crystalviewer/index.html.

* cited by examiner (a)

```
6
octahedron
O   1.000000   0.000000   0.000000
O   0.000000   1.000000   0.000000
O   0.000000   0.000000   1.000000
O  -0.000000  -0.000000  -1.000000
O  -0.000000  -1.000000   0.000000
O  -1.000000   0.000000   0.000000
```

(b)

(a)

```
#@ info dim = 3
#@ info size = 2
#@ info transitivity = 1112
#@ info selfdual = no
#@ info signature = 2[3^4] + [3^8]
#@ info group = Fm-3m
#@ info minimal = yes
#@ info net = fcu
#@ name #1
<1.1:2 3:1 2,1 2,1 2,2:3 3,3 4,4>
```

(b)

BRAVAIS LATTICE: CUBIC
SPACE GROUP: Fm3-m
SPACE GROUP NUMBER: 225

BRAVAIS LATTICE: TETRAGONAL
SPACE GROUP: I4/mmm
SPACE GROUP NUMBER: 139

D=0.0

D=0.00869

INFORMATION PROCESSING METHOD, INFORMATION PROCESSING SYSTEM, AND RECORDING MEDIUM

BACKGROUND

1. Technical Field

The present disclosure relates to a technique of generating a three-dimensional structure and others.

2. Description of the Related Art

Space-filling (tiling or tessellation) refers to operation of filling a space with figures without any gaps. For example, space-filling in a two-dimensional space is called plane filling, which refers to operation of filling a two-dimensional space with two-dimensional figures without any gaps.

Japanese Unexamined Patent Application Publication (Translation of PCT Application) No. 2018-516794 (hereinafter referred to as Patent Literature 1) discloses a method for generating a three-dimensional shape.

Kengo, N., & Takahide, M. (2016). How to describe disordered structures, Scientific Reports, 6, 23455. (hereinafter referred to as Non-Patent Literature 1) discloses a polyhedron code and a polychoron code.

SUMMARY

One non-limiting and exemplary embodiment provides an information processing method that makes it possible to generate a space-filled structure in a three-dimensional space, and others.

In one general aspect, the techniques disclosed here feature an information processing method executed by a computer, including acquiring first information concerning polyhedra; generating second information concerning a three-dimensional structure in which the polyhedra are arranged on the basis of the first information; and outputting the second information thus generated, in which the three-dimensional structure is a structure in which the polyhedra are arranged without any gaps and becomes a crystal structure in a case where atoms are arranged.

According to the present disclosure, it is possible to generate a space-filled structure in a three-dimensional space.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTIONS

Underlying Knowledge Forming Basis of the Present Disclosure

Conventionally, many space-filled structures in two-dimensional spaces have been found. On the other hand, there are unknown space-filled structures even in two-dimensional spaces, which have a long history of application. For example, recently, a new space-filled structure in a two-dimensional space using pentagons was reported.

Furthermore, there are space-filled structures in three-dimensional spaces in addition to space-filled structures in two-dimensional spaces. Hereinafter, a space-filled structure in a three-dimensional space is referred to as a "three-dimensional structure". The three-dimensional structure is such a structure that a three-dimensional space is filled with solid figures such as polyhedra without any gaps. In particular, the three-dimensional structure refers to such a structure that a three-dimensional space is filled with polyhedra without any gaps and becomes a crystal structure in a case where atoms are arranged. That is, the three-dimensional structure may be a crystal structure or may be a structure that can express a crystal structure. Note that the expression "filled with polyhedra without any gaps" means that each of the polyhedra is arranged so that each vertex of a face thereof that is in contact with another polyhedron is at the same height as a corresponding vertex of a face of the other polyhedron that is in contact with the polyhedron.

Furthermore, recently, application of the three-dimensional structure as a way of expressing a material structure is starting. The material structure is specifically a micro structure of a material such as a crystal material or an amorphous material, or the like. In particular, in a structure of an inorganic material, an atom is coordinated with adjacent atoms and is surrounded by these atoms. A structure of an inorganic material is configured such that a three-dimensional space is filled with polyhedra (coordination polyhedra) formed by connecting centers of adjacent atoms without any gaps. That is, a structure of an inorganic material can be regarded as a three-dimensional structure.

Figure 1:
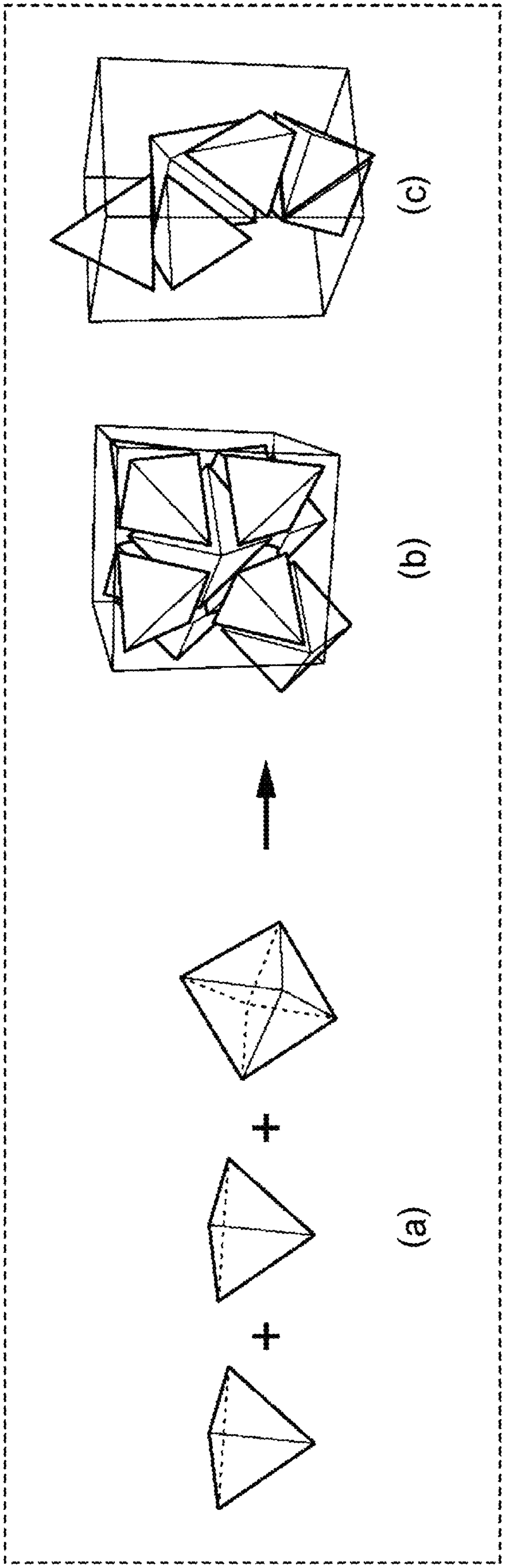
FIG. 1 illustrates an example of a three-dimensional structure generated from polyhedra.
Figure 2:
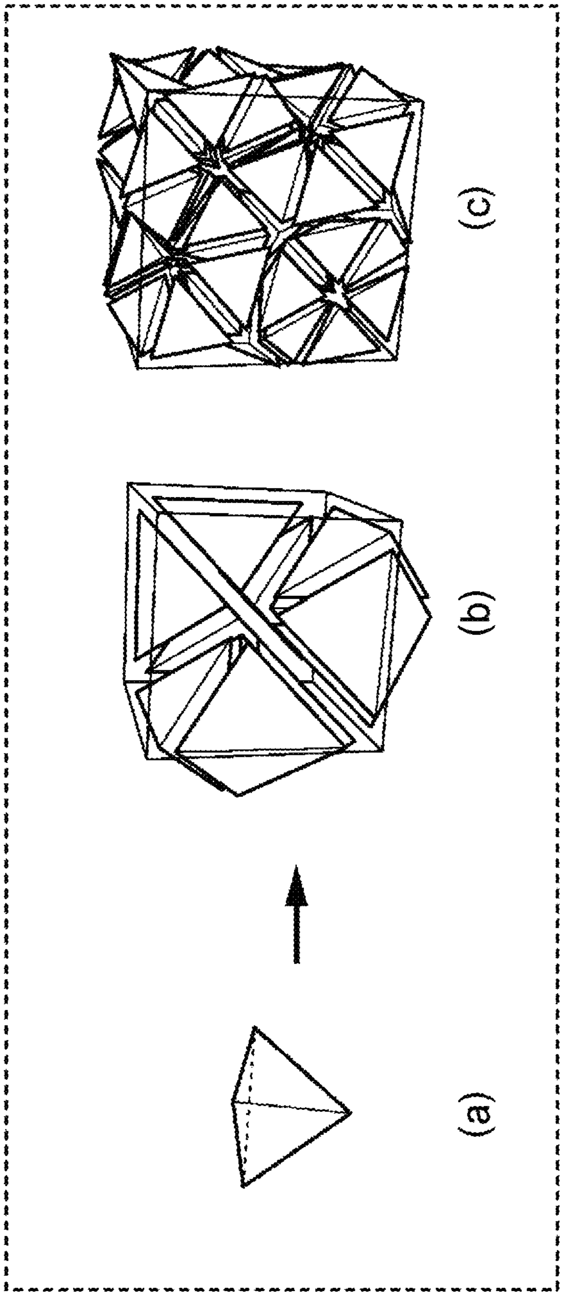
FIG. 2 illustrates another example of a three-dimensional structure generated from polyhedra.
Figure 3:
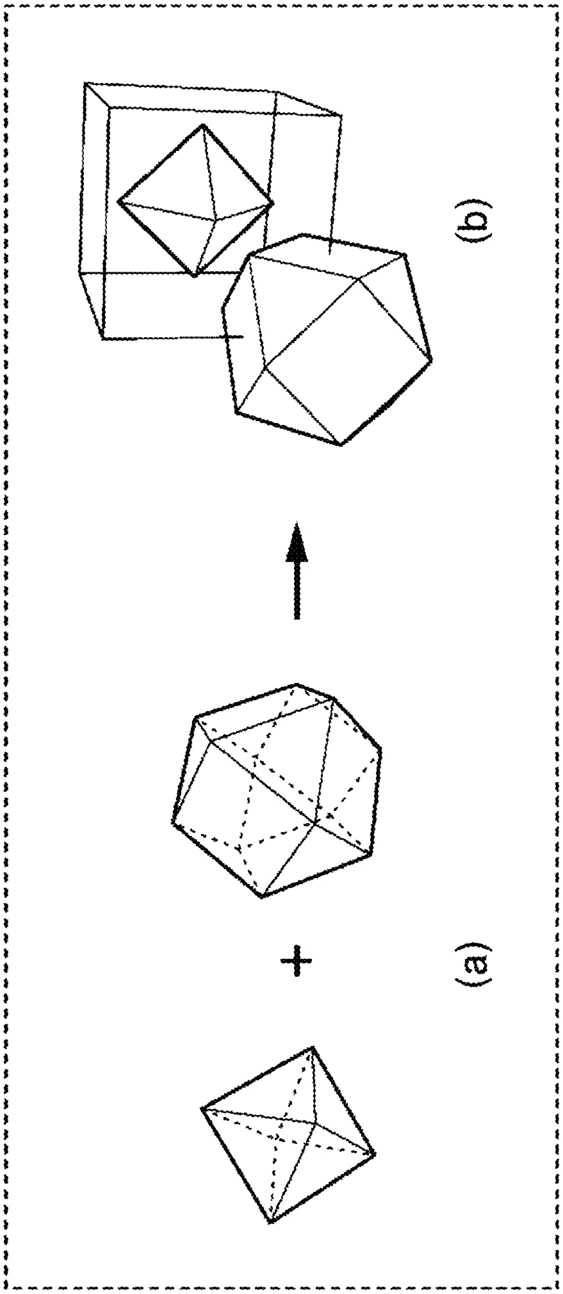
FIG. 3 illustrates still another example of a three-dimensional structure generated from polyhedra.

There are a wide variety of three-dimensional structures since there are a wide variety of combinations of filling coordination polyhedra. FIG. 1 illustrates an example of a three-dimensional structure generated from polyhedra. For example, there are two kinds of three-dimensional structures generated from two regular tetrahedra and one regular octahedron illustrated in FIG. 1(*a*) due to a difference in stacking, specifically, a face-centered cubic lattice structure (fcc-type structure) illustrated in FIG. 1(*b*) and a hexagonal close-packed structure (hcp-type structure) illustrated in FIG. 1(*c*). FIG. 2 illustrates another example of a three-dimensional structure generated from polyhedra. For example, there are two kinds of three-dimensional structures generated from one regular tetrahedron illustrated in FIG. 2(*a*) due to a difference in stacking, specifically, a body-centered cubic lattice structure (bcc-type structure) illustrated in FIG. 2(*b*) and a $MgCu_2$-type structure illustrated in FIG. 2(*c*). FIG. 3 illustrates a still another example of a three-dimensional structure generated from polyhedra. For example, there is a perovskite structure illustrated in FIG. 3(*b*) as a three-dimensional structure generated from one regular octahedron and one cuboctahedron illustrated in FIG. 3(*a*). Note that although one cuboctahedron is illustrated in FIG. 3(*b*), cuboctahedra are actually arranged around the regular octahedron at the center without any gaps.

However, it is difficult to find an unknown three-dimensional structure.

For example, Patent Literature 1 discloses a method for generating a three-dimensional space figure that permits a gap. However, Patent Literature 1 does not disclose a method for generating a three-dimensional structure in which polyhedra are arranged without any gaps.

Furthermore, Non Patent Literature 1 discloses a polyhedron code that describes a polyhedron as a numerical sequence and a polychoron code that describes a polychoron as a numerical sequence. However, Non Patent Literature 1 does not disclose a technique of generating a three-dimensional structure in which polyhedral are arranged without any gaps by using these.

In order to solve the above problem, an information processing method according to an aspect of the present disclosure is an information processing method executed by a computer, including acquiring first information concerning polyhedra; generating second information concerning a three-dimensional structure in which the polyhedra are arranged on the basis of the first information; and outputting the second information thus generated, in which the three-dimensional structure is a structure in which the polyhedra are arranged without any gaps and becomes a crystal structure in a case where atoms are arranged.

This makes it possible to generate a space-filled structure in a three-dimensional space.

For example, the second information may include at least one of information indicative of the three-dimensional structure, information indicative of a numerical sequence including a numeral or a character representing the three-dimensional structure, or information indicative of a periodic graph representing the three-dimensional structure.

This makes it possible to generate a space-filled structure in a three-dimensional space.

For example, in the acquiring the first information, unit structure information indicative of a shape of a unit structure in which the polyhedra are arranged without any gaps may be acquired as the first information, and in the generating the second information, the second information concerning the three-dimensional structure in which at least one unit structure indicated by the unit structure information is arranged may be generated.

This makes it possible to generate a space-filled structure in a three-dimensional space, for example, under restriction of a unit structure designated by a user, thereby making it easy to generate a space-filled structure in a three-dimensional space desired by the user.

The unit structure information may be information indicative of a Bravais lattice in the crystal structure.

This makes it possible to generate a space-filled structure in a three-dimensional space, for example, under restriction of a Bravais lattice designated by a user, thereby making it easy to generate a space-filled structure in a three-dimensional space desired by the user.

In the acquiring the first information, symmetry information indicative of symmetry of the three-dimensional structure may be acquired as the first information, and in the generating the second information, the second information concerning the three-dimensional structure having the symmetry indicated by the symmetry information may be generated.

This makes it possible to generate a space-filled structure in a three-dimensional space, for example, under restriction of symmetry designated by a user, thereby making it easy to generate a space-filled structure in a three-dimensional space desired by the user.

The symmetry information may be information indicative of a space group in the crystal structure.

This makes it possible to generate a space-filled structure in a three-dimensional space, for example, under restriction of a space group designated by a user, thereby making it easy to generate a space-filled structure in a three-dimensional space desired by the user.

In the acquiring the first information, shape information indicative of shapes of the polyhedra may be acquired as the first information, and in the generating the second information, the second information concerning the three-dimensional structure in which the polyhedra having the shapes indicated by the shape information are arranged without any gaps may be generated.

This makes it possible to generate a space-filled structure in a three-dimensional space, for example, under restriction of shapes of polyhedra designated by a user, thereby making it easy to generate a space-filled structure in a three-dimensional space desired by the user.

In the acquiring the first information, number information indicative of the number of polyhedra for each shape may be further acquired as the first information, and in the generating the second information, the second information concerning the three-dimensional structure in which the polyhedra having the shapes indicated by the shape information are arranged without any gaps so that the number of polyhedral of each shape becomes the number indicated by the number information may be generated.

This makes it possible to generate a space-filled structure in a three-dimensional space, for example, under restriction of the number of polyhedra for each shape designated by a user, thereby making it easy to generate a space-filled structure in a three-dimensional space desired by the user.

In the acquiring the first information, composition ratio information indicative of a composition ratio of the polyhedra based on the shapes may be further acquired as the first information, and in the generating the second information, the second information concerning the three-dimensional structure in which the polyhedra having the shapes indicated by the shape information are arranged without any gaps at the composition ratio based on the shapes indicated by the composition ratio information may be generated.

This makes it possible to generate a space-filled structure in a three-dimensional space, for example, under restriction of a composition ratio of polyhedra based on shapes designated by a user, thereby making it easy to generate a space-filled structure in a three-dimensional space desired by the user.

In the acquiring the first information, distortion degree information indicative of a permitted degree of distortion of the shapes of the polyhedra may be further acquired as the first information, and in the generating the second information, the second information concerning the three-dimensional structure in which at least one of the polyhedra is distorted so that the distortion does not exceed the degree of distortion indicated by the distortion degree information may be generated.

This makes it possible to generate a space-filled structure in a three-dimensional space, for example, under restriction of a degree of distortion of shapes of polyhedra designated by a user, thereby making it easy to generate a space-filled structure in a three-dimensional space desired by the user.

The degree of distortion may be decided on the basis of at least one of a position of a center of gravity of the polyhedron, a position of at least one vertex of the polyhedron, a length of at least one side of the polyhedron, an angle formed by at least two sides of the polyhedron, or an area of at least one face of the polyhedron while using a shape of the polyhedron indicated by the shape information as a reference.

This makes it possible to generate a space-filled structure in a three-dimensional space, for example, under restriction of a permitted degree of distortion of shapes of polyhedra designated by a user, thereby making it easy to generate a space-filled structure in a three-dimensional space desired by the user.

The generating the second information may include converting the acquired first information into first numerical sequences representing the polyhedra and converting a second numerical sequence representing a polychoron generated by using the first numerical sequences thus obtained into the three-dimensional structure.

This makes it possible to exhaustively generate a space-filled structure in a three-dimensional space from information of polyhedra.

The generating the second information may include converting the acquired first information into polyhedron graphs representing the polyhedra and converting a periodic graph generated by using the polyhedron graphs thus obtained into the three-dimensional structure.

This makes it possible to exhaustively generate a space-filled structure in a three-dimensional space from information of polyhedra by various methods.

In the acquiring the first information, material information concerning a composition of a material may be acquired as the first information.

This makes it possible to generate a space-filled structure in a three-dimensional space concerning a material which a user wants to search for.

The material information may include at least one of an atom contained in the material or the composition of the material, in the acquiring the first information, arrangement information concerning an arrangement of the atom in the three-dimensional structure may be further acquired as the first information, and in the generating the second information, the second information concerning the three-dimensional structure may be generated on the basis of the arrangement of the atom indicated by the arrangement information.

This makes it possible to generate a space-filled structure in a three-dimensional space concerning a material which a user wants to search for.

The three-dimensional structure generated in the generating the second information may be the crystal structure which the composition of the material can take.

This makes it possible to generate a crystal structure concerning a material which a user wants to search for.

An information processing system according to an aspect of the present disclosure includes a display that displays a first image for receiving first information concerning polyhedra; and a display controller that causes a second image showing second information concerning a three-dimensional structure in which the polyhedra are arranged to be displayed on the display, the second information being generated on the basis of the input first information, in which the three-dimensional structure is a structure in which the polyhedra are arranged without any gaps and becomes a crystal structure in a case where atoms are arranged.

This allows a user to check a generated space-filled structure in a three-dimensional space.

A recording medium according to an aspect of the present disclosure is a non-volatile computer-readable recording medium storing a program causing a computer to perform processing including acquiring first information concerning polyhedra; generating second information concerning a three-dimensional structure in which the polyhedra are arranged on the basis of the first information; and outputting the second information thus generated, in which the three-dimensional structure is a structure in which the polyhedra are arranged without any gaps and becomes a crystal structure in a case where atoms are arranged.

This makes it possible to generate a space-filled structure in a three-dimensional space.

The present disclosure may be realized as a computer program that causes a computer to perform the characteristic processing included in the information processing method of the present disclosure. Needless to say, such a computer program can be distributed on a computer-readable non-transitory recording medium such as a CD-ROM or over a communication network such as the Internet.

That is, according to the technique of the present disclosure, by inputting information on polyhedra, it is possible to exhaustively generate a three-dimensional structure made up of the input polyhedra. This information processing method is more effective for searching for a material.

A physical property of a material such as electron conduction, ion conduction, or heat conduction greatly depends on how an atom is coordinated with surrounding atoms, that is, an atom's local coordination environment. For example, in a case of an ionic crystal material, a cation is surrounded by a group of anions. A polyhedron formed by connecting centers of these anions is called a coordination polyhedron. For example, AgI takes a fcc-type structure of low Ag ion conductivity and a bcc-type structure of high Ag ion conductivity. In the fcc-type structure, I ions around an Ag ion are formed in such a manner that the structure is filled with a coordination polyhedron made up of a tetrahedron and an octahedron. Since the Ag ion is stable in an octahedral site and therefore cannot move to an adjacent tetrahedral site, the Ag ion is hard to conduct. On the other hand, in the bcc-type structure, the I ions around the Ag ion are formed in such a manner that the structure is filled with a coordination polyhedron made up of tetrahedra. Since all sites are equivalent, the Ag ion easily conducts.

As just described, a physical property that a material exhibits differs depending on a kind of filling coordination polyhedron. Therefore, if a crystal structure can be generated while designating a high-function coordination polyhedron, an unknown material can be efficiently searched for. That is, a crystal structure that has not been reported before can be generated, and an unknown high-function material can be found. Since a structure of an inorganic material can be regarded as a three-dimensional structure, the technique of the present disclosure that can generate a three-dimensional structure upon input of information on polyhedra is very effective for searching for an unknown material.

Embodiments are specifically described below with reference to the drawings.

Each of the embodiments described below illustrates a general or specific example of the present disclosure. Numerical values, shapes, materials, constituent elements, the way in which the constituent elements are disposed and connected, steps, the order of steps, and the like illustrated in the embodiments below are examples and do not limit the present disclosure. Among constituent elements in the embodiments below, constituent elements that are not described in independent claims indicating highest concepts are described as optional constituent elements. Furthermore, contents in the embodiments may be combined in all the embodiments. Each drawing is a schematic view and is not necessarily strict illustration. In the drawings, identical constituent elements are given identical reference signs.

An information processing system according to an embodiment of the present disclosure may be configured such that all constituent elements are included in a single computer or may be configured as a system in which constituent elements are distributed into computers.

Embodiment 1

An information processing system 100 (an information processing method, or a recording medium) according to Embodiment 1 of the present disclosure is described in detail below with reference to the drawings.

Generation of Three-Dimensional Structure

First, before detailed description of Embodiment 1, generation of a three-dimensional structure in an information processing method of the present disclosure is described. In the information processing method of the present disclosure, a three-dimensional structure is exhaustively generated by expressing a three-dimensional structure as a numerical sequence or a graph. Note that the "numerical sequence" as used herein includes not only a numeral, but also a character replacing a numeral, such as an alphabet.

Hereinafter, a numerical sequence expressing a three-dimensional structure is sometimes referred to as an "inorganic gene". Examples of the inorganic gene include a polychoron code proposed by K. Nishio et al., SystreKey or D-Symbol proposed by O. Delgado-Friedrichs et al., and CRYSTAL-SELFIES proposed by M. Krenn et al., which is application of SELFIE that can express a molecular structure as an alphabet sequence to a three-dimensional structure. In other words, the inorganic gene is, for example, a polychoron code that can be converted into a three-dimensional structure.

For example, a polychoron code of a zeolite A (LTA) structure is expressed as a numerical sequence "$OHG^4(HG)^4H$". Note that "O", "H", and "G" in the numerical sequence are called polyhedron codes and are numerical sequences decided on the basis of input polyhedra. For example, "O" means a truncated octahedron and is expressed as a numerical sequence "$46^4(46)^44$". Furthermore, for example, "H" means a cube and is expressed as a numerical sequence "46". Furthermore, for example, "G" means a truncated cuboctahedron and is expressed as a numerical sequence "$6(48)^3(64)^6(84)^36$".

By rearranging the polychoron code, another three-dimensional structure made up of the same polyhedra can be generated. Furthermore, by changing a polyhedron code, any polyhedron can be expressed. By thus using an inorganic gene represented by a polychoron code, a three-dimensional structure can be exhaustively generated from information on polyhedra.

Figure 4:
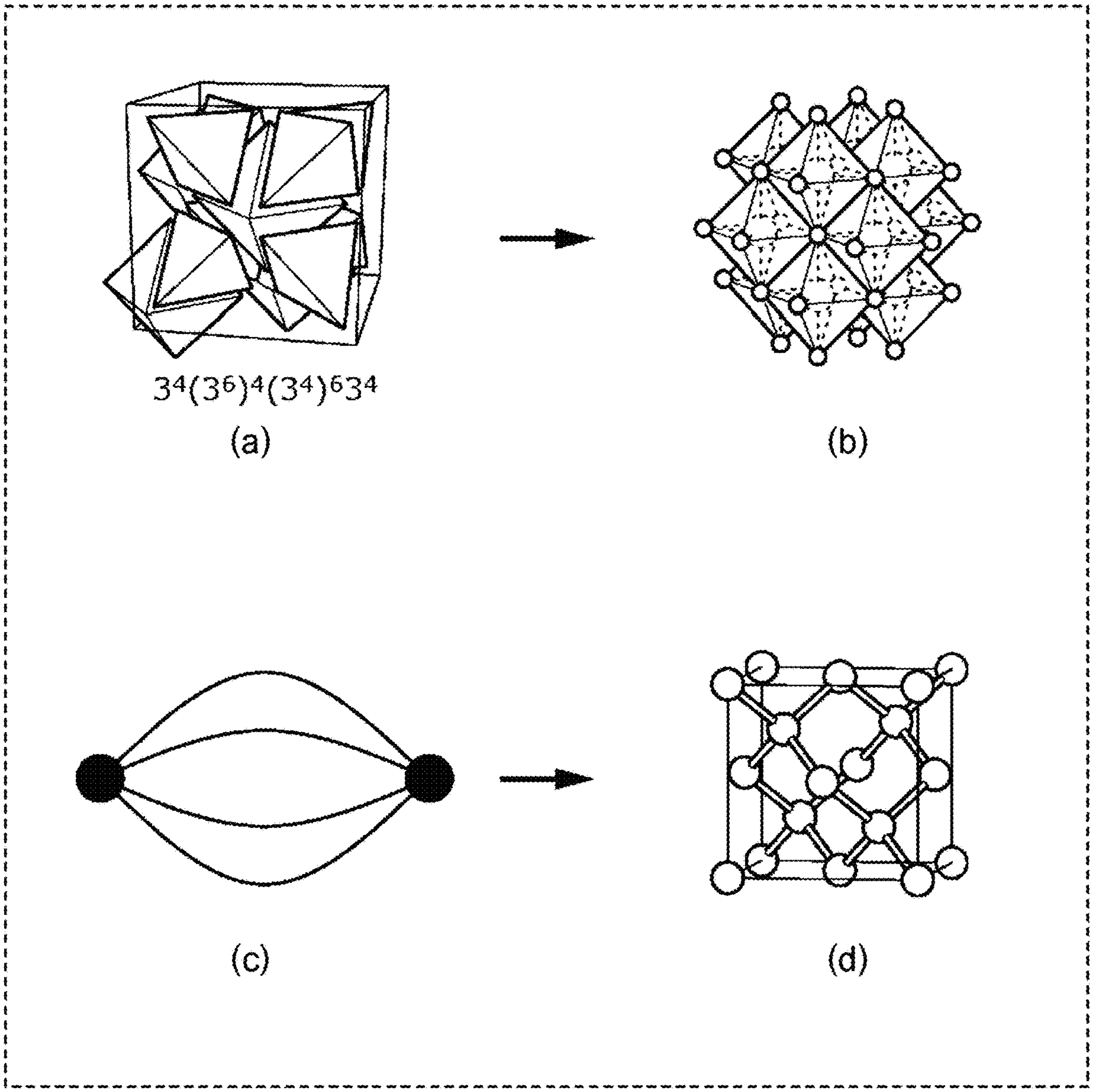
FIG. 4 illustrates an example of a crystal structure generated from a three-dimensional structure.

By arranging atoms at a center of each polyhedron and vertexes of each polyhedron as appropriate in the three-dimensional structure thus generated, a crystal structure can be generated from the three-dimensional structure. FIG. 4 illustrates an example of a crystal structure generated from a three-dimensional structure. For example, a crystal structure illustrated in FIG. 4(*b*) can be generated from a three-dimensional structure illustrated in FIG. 4(*a*) (expressed as "$3^4(3^6)^4(3^4)^63^4$" in a polychoron code).

In general, a molecular structure can be expressed as a graph. That is, a molecular structure can be expressed as a graph structure expressing "atoms" constituting a compound as "nodes" and expressing "a bond between atoms" as an "edge" connecting the nodes. For example, an example in which a molecular structure is generated by expressing the molecular structure as a graph is disclosed in Japanese Unexamined Patent Application Publication No. 2021-081769.

On the other hand, a crystal structure needs to be expressed not by a normal graph, but by a periodic graph. The periodic graph is also called a crystal net and is a three-dimensionally periodic graph. The expression "three-dimensionally periodic" means that three linear independent translations exist. In general, by defining an atomic bond in a crystal structure, the crystal structure can be converted into a periodic graph. Furthermore, a periodic graph can be uniquely converted into a crystal structure by using the Kotani-Sunada theory (Kotani-Sunada, 2000, Trans. Amer. Mat). For example, as illustrated in FIG. 4(*c*), a periodic graph having two independent nodes and four edges connecting these nodes are interchangeable with a diamond-like structure illustrated in FIG. 4(*d*). In other words, the periodic graph is a graph that can be converted into a three-dimensional structure that has a structure in which polyhedra are arranged without any gaps and becomes a crystal structure in a case where atoms are arranged.

Information Processing System

Next, a configuration of the information processing system used in Embodiment 1 is described.

Figure 5:
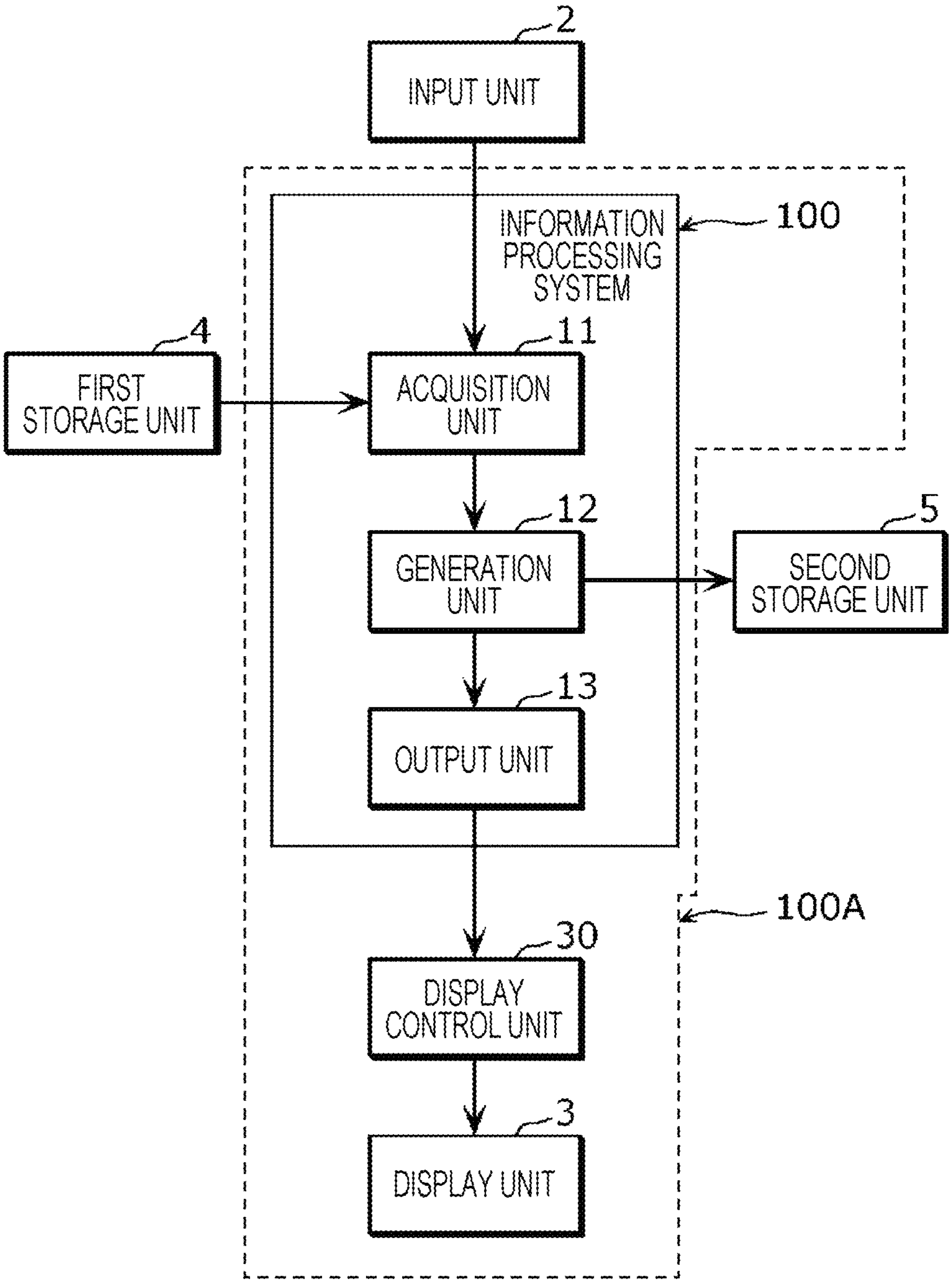
FIG. 5 is a block diagram illustrating an overall configuration including an information processing system according to Embodiment 1.

FIG. 5 is a block diagram illustrating an overall configuration including the information processing system 100 according to Embodiment 1. The information processing system 100 is, for example, a computer such as a personal computer or a server. That is, the information processing system 100 may be, for example, realized by cloud computing. In Embodiment 1, it is assumed that the information processing system 100 is a desktop computer.

The information processing system 100 includes an acquisition unit 11, a generation unit 12, and an output unit 13. Furthermore, to the information processing system 100, an input unit 2, a display control unit 30, a display unit 3, a first storage unit 4, and a second storage unit 5 are connected. The input unit 2, the display control unit 30, and the display unit 3 are, for example, realized by an information terminal used by a user such as a smartphone, a tablet terminal, or a personal computer. The input unit 2, the display control unit 30, and the display unit 3 may be an input unit, a display control unit, and a display unit included in an information terminal used by a user.

The input unit 2, the display control unit 30, the first storage unit 4, and the second storage unit 5 may be connected to the information processing system 100 over a Local Area Network (LAN) or may be connected to the information processing system 100 over a network such as the Internet.

The input unit 2 is an input interface that receives user's input and is, for example, a keyboard, a touch sensor, a touch pad, a mouse, or the like. The input unit 2 receives user's input operation and outputs a signal according to the input operation to the information processing system 100. Although the display unit 3 and the input unit 2 are independent of each other in the present disclosure, the display unit 3 and the input unit 2 may be integral with each other (e.g., a touch panel). Furthermore, although the information processing system 100 includes neither the display unit 3 nor the input unit 2 in the present disclosure, the information processing system 100 may include the display unit 3 and the input unit 2.

The input unit 2 receives input of first information concerning polyhedra. The first information can include, for example, kinds of polyhedra, the number of polyhedra, a permitted degree of distortion, permitted symmetry, or the like. Details of the first information and input of the first information using the input unit 2 will be described later.

The display control unit 30 causes an image or the like to be displayed on the display unit 3 on the basis of information output from the output unit 13 of the information processing system 100.

The display unit 3 displays an image or the like under control of the display control unit 30. The display unit 3 is, for example, a liquid crystal display, a plasma display, an organic Electro-Luminescence (EL), or the like, but is not limited to this.

The first storage unit 4 is a recording medium in which a polyhedron database is stored. The recording medium is, for example, a hard disk drive, a Random Access Memory (RAM), a Read Only Memory (ROM), a semiconductor memory, or the like. Note that such a recording medium may be volatile or may be non-volatile. The polyhedron database includes data concerning a polyhedron such as a figure of the polyhedron, the number of vertexes of the polyhedron, the number of sides of the polyhedron, the number of faces of the polyhedron, or a shape of a face of the polyhedron. Examples of the polyhedra included in the polyhedron database include regular polyhedra such as a regular tetrahedron, a regular hexahedron, a regular octahedron, a regular dodecahedron, and a regular icosahedron. Other examples of the polyhedra include semi-regular polyhedra such as a truncated tetrahedron, a truncated hexahedron, a truncated octahedron, a truncated dodecahedron, a truncated icosahedron, a cuboctahedron, an icosidodecahedron, a rhombicuboctahedron, a rhombicosidodecahedron, a rhombitruncated cuboctahedron, a rhombitruncated icosidodecahedron, a snub cube, and a snub dodecahedron. The polyhedron data is used when the user input the first information by the input unit 2.

Figure 6:
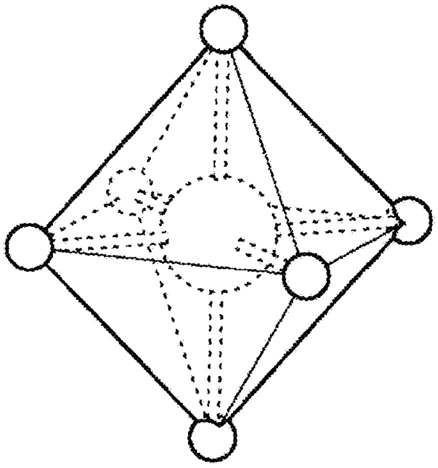
FIG. 6 illustrates an example of polyhedron data stored in a first storage unit.

FIG. 6 illustrates an example of polyhedron data stored in the first storage unit 4. FIG. 6(*a*) illustrates a structure of a polyhedron (a regular octahedron in this example), and FIG. 6(*b*) illustrates data in which the structure of the polyhedron illustrated in FIG. 6(*a*) is described in a predetermined description format (an xyz file format in this example). In the first storage unit 4, for example, an image showing a structure of a polyhedron such as the one illustrated in FIG. 6(*a*) and data described in a predetermined description format such as the one illustrated in FIG. 6(*b*) are stored as polyhedron data.

The second storage unit 5 is a recording medium in which second information concerning a three-dimensional structure generated by the generation unit 12 is stored. The recording medium is, for example, a hard disk drive, a Random Access Memory (RAM), a Read Only Memory (ROM), a semiconductor memory, or the like. Note that such a recording medium may be volatile or may be non-volatile.

Figure 7:
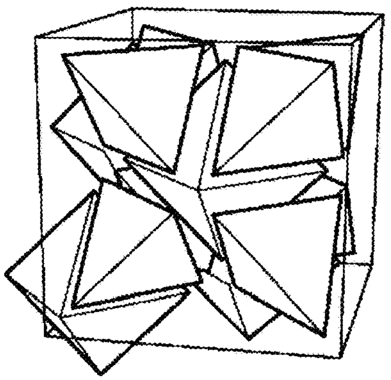
FIG. 7 illustrates an example of second information stored in a second storage unit.

FIG. 7 illustrates an example of the second information stored in the second storage unit 5. FIG. 7(*a*) illustrates a three-dimensional structure (a fcc-type structure in this example) indicated by the second information, and FIG. 7(*b*) illustrates data in which the three-dimensional structure illustrated in FIG. 7(*a*) is described in a predetermined description format (a D-Symbol format in this example). In the second storage unit 5, for example, an image showing a three-dimensional structure such as the one illustrated in FIG. 7(*a*) and data described in a predetermined description format such as the one illustrated in FIG. 7(*b*) are stored as the second information. The second information includes, for example, three-dimensional data, graph data, a space group, a Wyckoff label, a cell size, coordinates, maximum distortion of a polyhedron, or the like.

A file format (extension) of data stored in the second storage unit 5 is, for example, *.sldprt, *.sldasm, *.iam, *.ipt, *.model, *.CATPart, *.CATProduct, *.3ds, *.max, or the like. As for the file format (extension), see the website indicated by a URL "https://www.data-henkan.com/extension-list".

The acquisition unit 11 acquires first information concerning polyhedra. The acquisition unit 11 is a unit that executes a step of acquiring the first information in the information processing method of the present disclosure. Specifically, the acquisition unit 11 acquires the first information input by the user by the input unit 2. The user performs operation of inputting the first information while seeing a first image for receiving the first information displayed on the display unit 3, as described later.

The generation unit 12 generates second information concerning a three-dimensional structure in which polyhedra are arranged on the basis of the first information acquired by the acquisition unit 11. The generation unit 12 is a unit that executes a step of generating the second information in the information processing method according to the present disclosure. In Embodiment 1, the generation unit 12 performs processing for converting the acquired first information into first numerical sequences each representing a polyhedron and processing for converting a second numerical sequence representing a polychoron generated by using the first numerical sequences into a three-dimensional structure. That is, the generation unit 12 performs processing for converting polyhedra into polyhedron codes (the first numerical sequences) and processing for converting a polychoron code (the second numerical sequence) generated by the polyhedron codes into a three-dimensional structure. Details of the above processing will be described later.

The output unit 13 causes an image or the like to be displayed on the display unit 3 by outputting the image or the like to the display control unit 30. Furthermore, the output unit 13 outputs the second information generated by the generation unit 12. The output unit 13 is a unit that executes a step of outputting the second information in the information processing method of the present disclosure. Specifically, the output unit 13 outputs the second information by causing a second image showing the second information generated by the generation unit 12 to be displayed on the display unit 3. The user performs operation of selecting the second information to be stored in the second storage unit 5 while seeing the second image displayed on the display unit 3, as described later.

Use Examples

Examples of use of the information processing system 100 according to Embodiment 1 are described below. To the information processing system 100, any one of first to fifth use examples described below may be applied or use examples may be applied in combination. In the description of the second to fifth use examples below, description of points identical to the first use example is omitted.

Figure 8B:
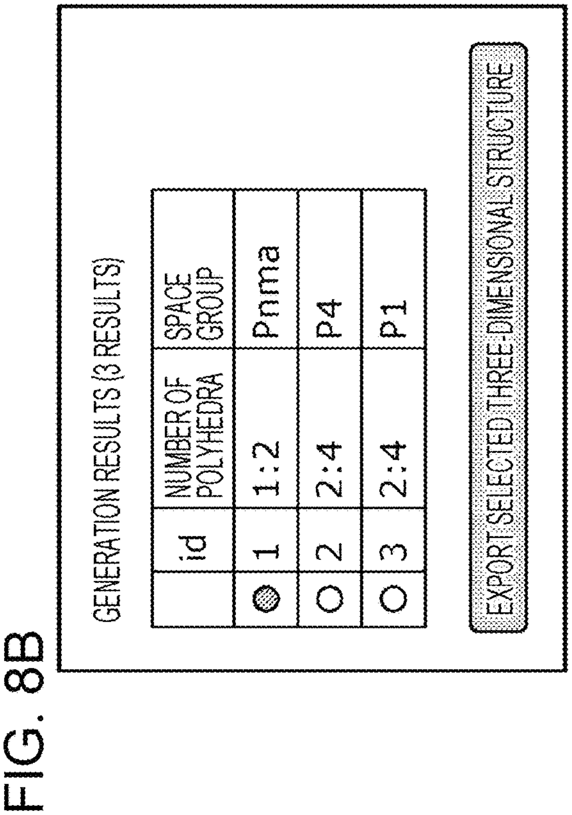
FIGS. 8A and 8B illustrate an image displayed on a display unit in a first use example of Embodiment 1.
Figure 8A:
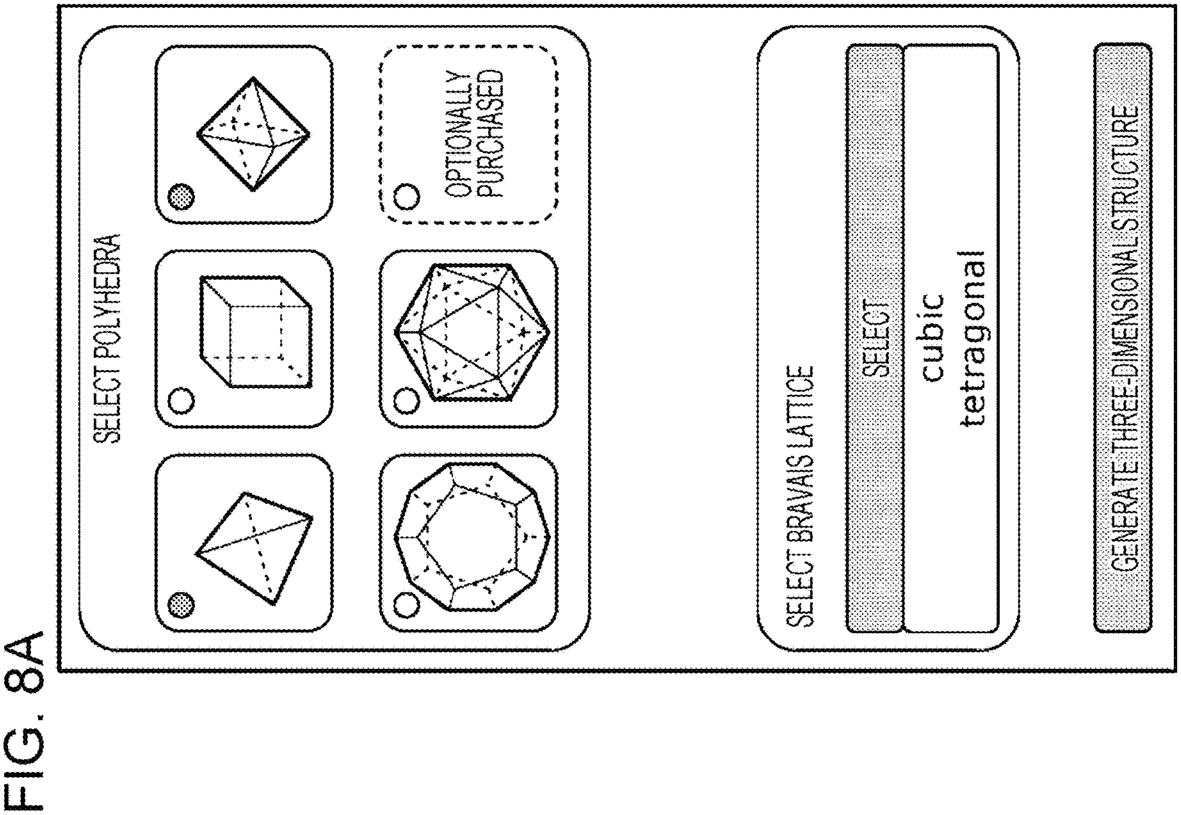

FIGS. 8A and 8B and 9A and 9B each illustrate an image displayed on the display unit 3 in the first use example of Embodiment 1. FIG. 8A illustrates an example of the first image displayed on the display unit 3. The first image is displayed on the display unit 3 by the output unit 13 by reading out polyhedron data stored in the first storage unit 4.

In the first use example, the first image includes a shape selection region for selecting a shape of a polyhedron, a unit structure selection region for selecting a unit structure (a Bravais lattice in this example), and an execution icon "GENERATE THREE-DIMENSIONAL STRUCTURE".

In the shape selection region, polyhedra that can be selected by a user, selection buttons corresponding to the polyhedra are displayed. In the shape selection region, names of shapes of the polyhedra may be displayed. In the shape selection region, each polyhedron may be displayed not as a still image, but as a moving image. In the shape selection region, the user selects polyhedra to be included in a three-dimensional structure. As a result, the acquisition unit 11 (in the step of acquiring the first information) acquires, as the first information, shape information indicative of shapes of the polyhedra. In this case, when the user selects the execution icon, the generation unit 12 (in the step of generating the second information) generates second information concerning a three-dimensional structure in which the polyhedra having the shapes indicated by the shape information are arranged without any gaps. In the example illustrated in FIG. 8A, the user selects a regular tetrahedron and a regular octahedron. Accordingly, in this case, the generation unit 12 generates second information concerning a three-dimensional structure in which a regular tetrahedron and a regular octahedron are arranged without any gaps.

Note that the user may increase kinds of selectable polyhedra, for example, by paying money to a business operator that runs the information processing system 100. In the example illustrated in FIG. 8A, a polyhedron newly made selectable by user's payment is displayed in a field with a caption "OPTIONALLY PURCHASED" in the shape selection region.

Figure 10:
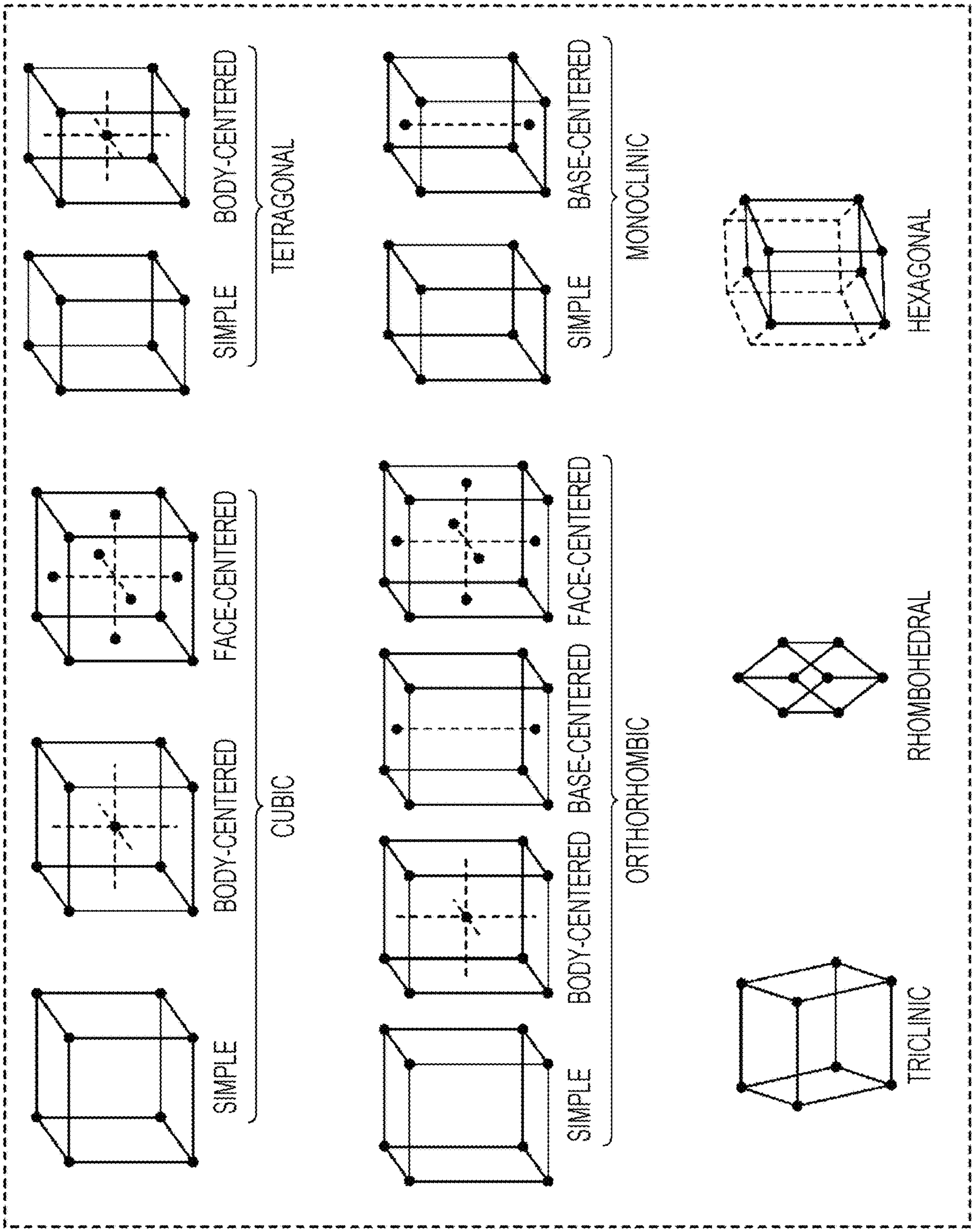
FIG. 10 illustrates a list of Bravais lattices.

In the unit structure selection region, kinds of unit structures (a Bravais lattice in this example) that can be selected by the user are displayed. Note that although the user can select any one of "cubic" and "tetragonal" in the example illustrated in FIG. 8A, one may be selectable from among the list of Bravais lattices illustrated in FIG. 10, for example. FIG. 10 illustrates the list of Bravais lattices.

The user selects a unit structure (a Bravais lattice in this example) in the unit structure selection region. As a result, the acquisition unit 11 (in the step of acquiring the first information) acquires, as the first information, unit structure information indicative of a shape of a unit structure in which polyhedra are arranged without any gaps. In this example, the unit structure information is information indicative of a Bravais lattice in a crystal structure. In this case, when the user selects the execution icon, the generation unit 12 (in the step of generating the second information) generates second information concerning a three-dimensional structure in which at least one unit structure (Bravais lattice in this example) indicated by the unit structure information is arranged.

FIG. 8B illustrates an example of the second image displayed on the display unit 3. The second image is displayed on the display unit 3 after the user selects the execution icon in the first image and the generation unit 12 generates second information concerning a three-dimensional structure. The second image includes a table showing a list of three-dimensional structures generated by the generation unit 12 and an execution icon "EXPORT SELECTED THREE-DIMENSIONAL STRUCTURE". The table shows, from the left, a column for selecting a three-dimensional structure to be exported, a column showing an identification number (ID) of each three-dimensional structure, a column showing the number of polyhedra included in the three-dimensional structure for each shape (a composition ratio in this example), and a column showing symmetry (a space group in this example) of the three-dimensional structure.

Figure 9A:
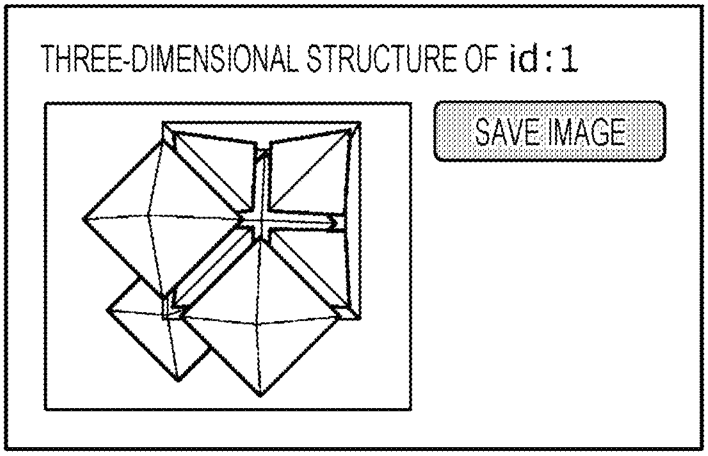
FIGS. 9A and 9B illustrate an image displayed on the display unit in the first use example of Embodiment 1.
Figure 9B:
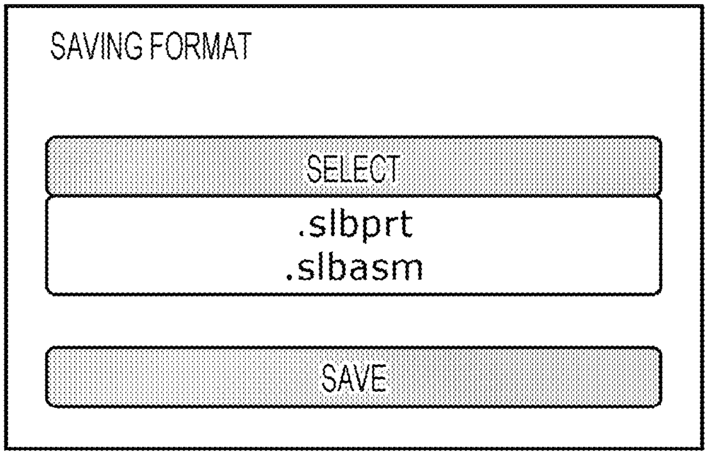

The user selects a three-dimensional structure to be saved and then selects the execution icon. As illustrated in FIG. 9A, an image including a region showing the selected three-dimensional structure and an execution icon "SAVE IMAGE" is thus displayed on the display unit 3. Then, the user checks the selected three-dimensional structure and, if there is no problem, selects the execution icon. As a result, an image including a selection region for selecting a saving format of the three-dimensional structure and an execution icon "SAVE" is displayed on the display unit 3, as illustrated in FIG. 9B. Although the user can select any one of ".slbprt" and ".slbasm" in the example illustrated in FIG. 9B, other saving formats may be selectable. When the user selects a desired saving format and then selects the execution icon, second information concerning the three-dimensional structure selected by the user is saved in the second storage unit 5.

Figure 11:
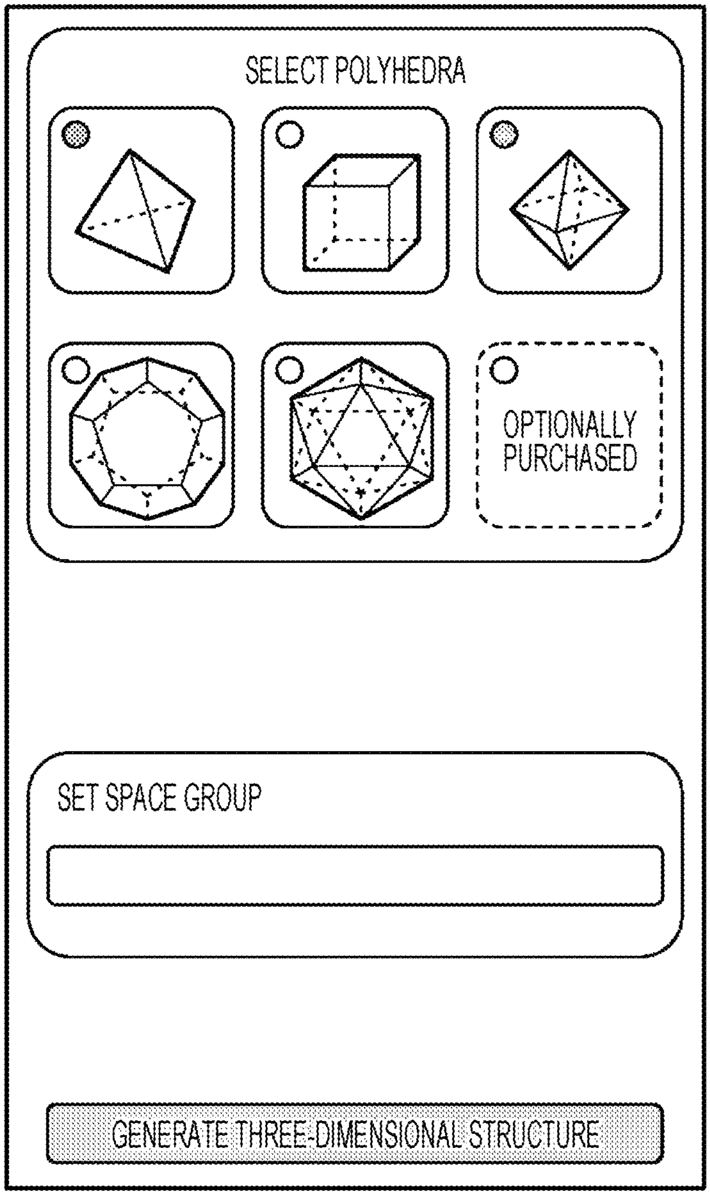
FIG. 11 illustrates an image displayed on the display unit in a second use example of Embodiment 1.

FIG. 11 illustrates an image displayed on the display unit 3 in the second use example of Embodiment 1. FIG. 11 illustrates an example of the first image displayed on the display unit 3. In the second use example, the first image includes a symmetry designation region for designating symmetry (a space group in this example) of a three-dimensional structure instead of the unit structure selection region, unlike the first use example.

Figure 12A:
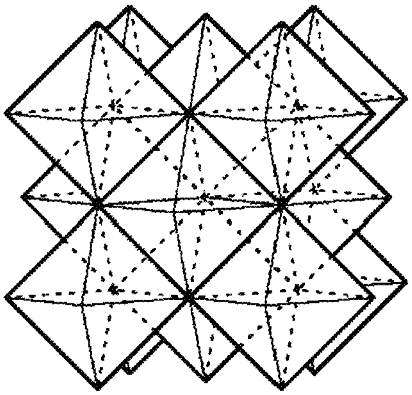
FIGS. 12A and 12B illustrate an example of symmetry of a three-dimensional structure.
Figure 12B:
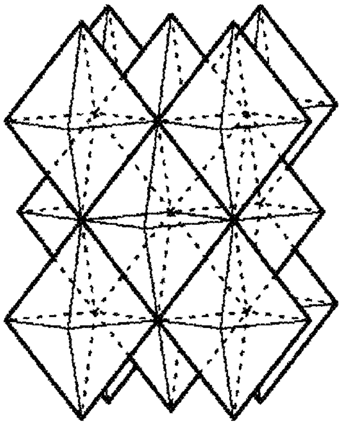

In the symmetry designation region, a textbox for designating symmetry (a space group in this example) of a three-dimensional structure desired by the user is displayed. The space group is used to describe symmetry of the three-dimensional structure. FIGS. 12A and 12B illustrate an example of symmetry of a three-dimensional structure. The three-dimensional structure illustrated in FIG. 12A has symmetry indicated by a space group "Fm3-m" given a space group number "225". The three-dimensional structure illustrated in FIG. 12B has symmetry indicated by a space group "14/mmm" given a space group number "139". As for space groups, see the website indicated by a URL "https:/en.wikipedia.org/wiki/List_of_space_groups".

The user designates symmetry of a three-dimensional structure by inputting a number of a desired space group in the textbox in the symmetry designation region. Note that a range of numbers of desired space groups may be input in the textbox. As a result, the acquisition unit 11 (in the step of acquiring the first information) acquires, as the first information, symmetry information indicative of symmetry of a three-dimensional structure. The symmetry information is information indicative of a space group in a crystal structure. In this case, when the user selects the execution icon, the generation unit 12 (in the step of generating the second information) generates second information concerning a three-dimensional structure having symmetry (a space group in this example) indicated by the symmetry information.

Note that in the second use example, space groups that can be selected by the user may be listed instead of the textbox in the symmetry designation region of the first image. In this case, the user need just select any one space group from among the space groups.

Figure 13:
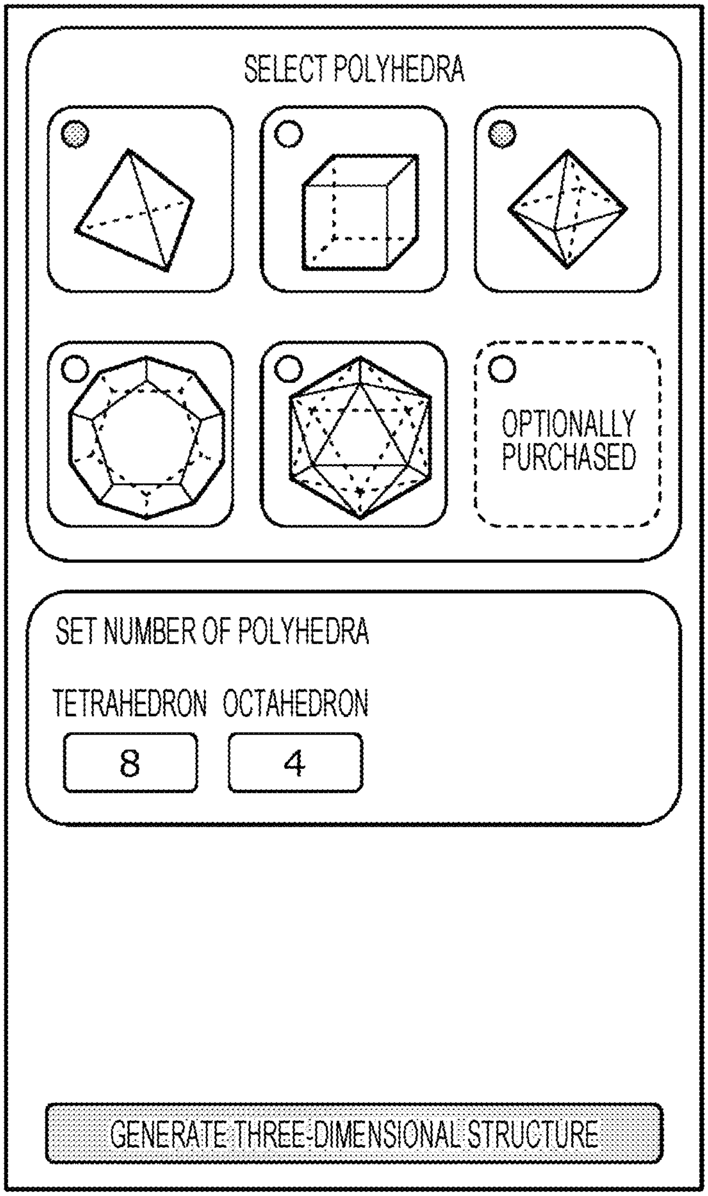
FIG. 13 illustrates an image displayed on the display unit in a third use example of Embodiment 1.

FIG. 13 illustrates an image displayed on the display unit 3 in the third use example of Embodiment 1. FIG. 13 illustrates an example of the first image displayed on the display unit 3. In the third use example, the first image includes a number designation region for designating the number of polyhedra to be included in a three-dimensional structure for each shape instead of the unit structure selection region, unlike the first use example.

In the number designation region, names of shapes of polyhedra selected in the shape selection region and a textbox for designating the number of polyhedra to be included in a three-dimensional structure are displayed. In the example illustrated in FIG. 13, the user selects a regular tetrahedron and a regular octahedron in the shape selection region. Accordingly, in the number designation region, a textbox for designating the number of regular tetrahedra and a textbox for designating the number of regular octahedra are displayed.

The user designates the number of polyhedra to be included in the three-dimensional structure by inputting a desired number in the textbox in the number designation region. As a result, the acquisition unit 11 (in the step of acquiring the first information) further acquires, as the first information, number information indicative of the number of polyhedra for each shape. In this case, when the user selects the execution icon, the generation unit 12 (in the step of generating the second information) generates second information concerning a three-dimensional structure in which polyhedra having shapes indicated by the shape information are arranged without any gaps so that the number of polyhedra of each shape becomes the number indicated by the number information.

Figure 14:
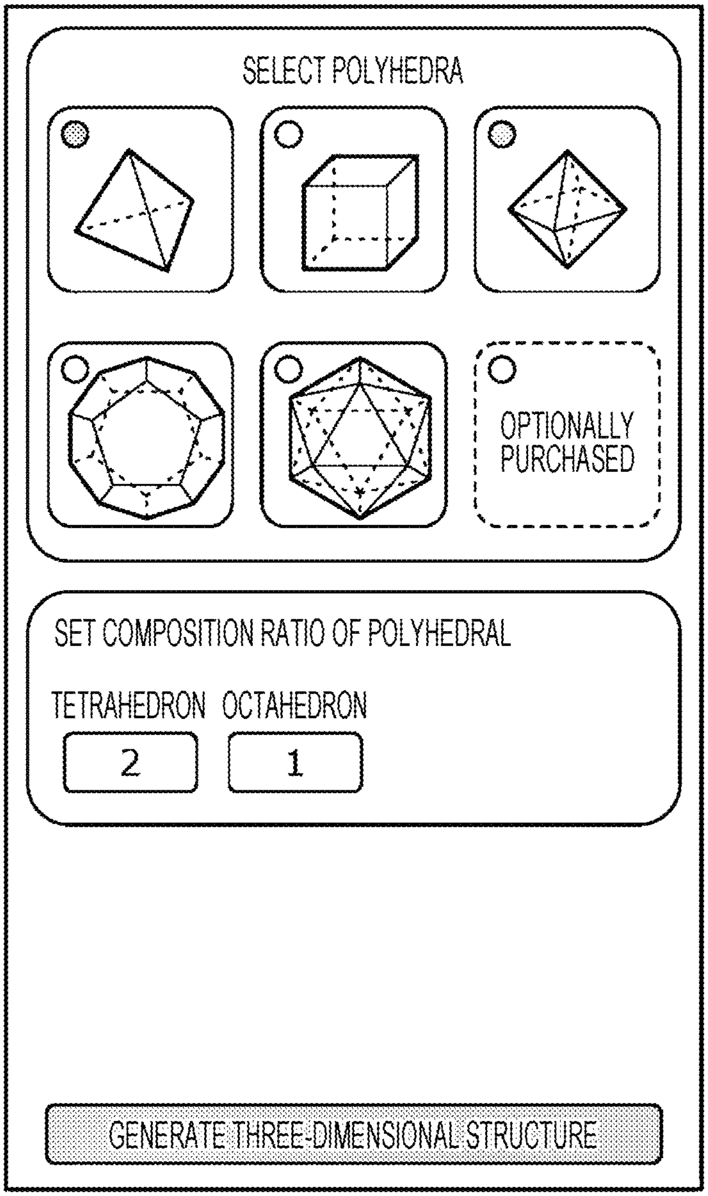
FIG. 14 illustrates an image displayed on the display unit in a fourth use example of Embodiment 1.

FIG. 14 illustrates an image displayed on the display unit 3 in the fourth use example of Embodiment 1. FIG. 14 illustrates an example of the first image displayed on the display unit 3. In the fourth use example, the first image includes a composition ratio designation region for designating a composition ratio of polyhedra to be included in a three-dimensional structure based on shapes instead of the unit structure selection region, unlike the first use example.

In the composition ratio designation region, names of shapes of polyhedra selected in the shape selection region and a textbox for designating a composition ratio of polyhedra to be included in a three-dimensional structure are displayed. In the example illustrated in FIG. 14, the user selects a regular tetrahedron and a regular octahedron in the shape selection region. Accordingly, in the composition ratio designation region, a textbox for designating a composition ratio of the regular tetrahedron and a textbox for designating a composition ratio of the regular octahedron are displayed.

The user designates a composition ratio of polyhedra to be included in a three-dimensional structure based on shapes by inputting a desired composition ratio in the textbox in the composition ratio designation region. As a result, the acquisition unit 11 (in the step of acquiring the first information) further acquires, as the first information, composition ratio information indicative of a composition ratio of polyhedra based on shapes. In this case, when the user selects the execution icon, the generation unit 12 (in the step of generating the second information) generates second information concerning a three-dimensional structure in which polyhedra having shapes indicated by shape information are arranged without any gaps at a composition ratio based on shapes indicated by the composition ratio information.

Figure 15B:
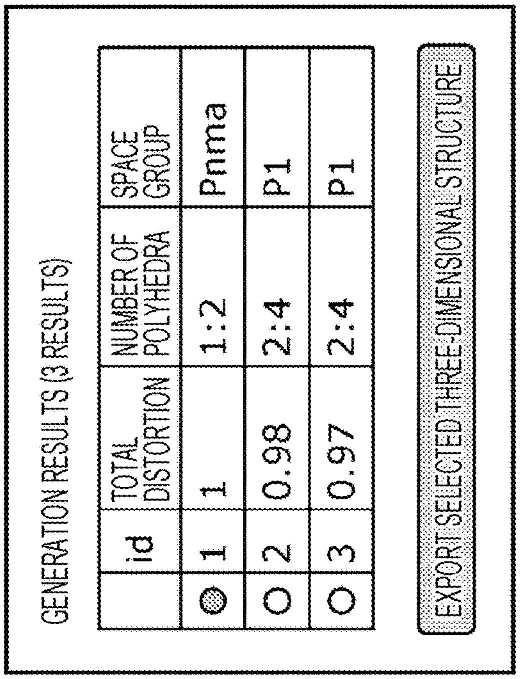
FIGS. 15A and 15B illustrate an image displayed on the display unit in a fifth use example of Embodiment 1.
Figure 15A:
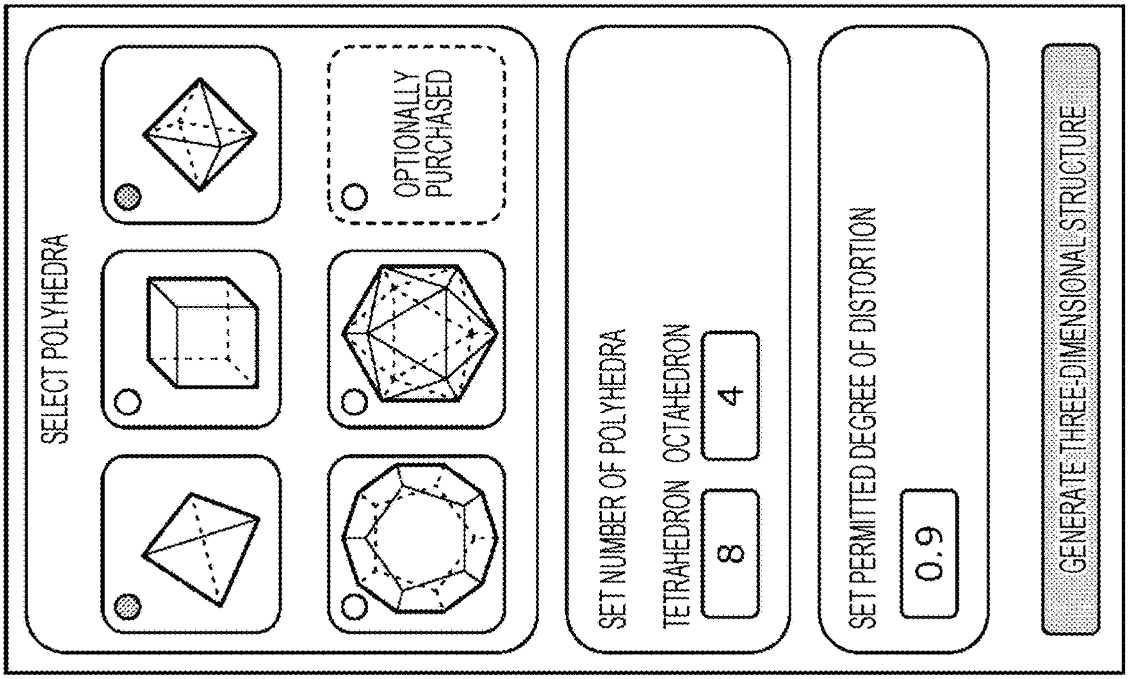

FIGS. 15A and 15B illustrate an image displayed on the display unit 3 in the fifth use example of Embodiment 1. FIG. 15A illustrates an example of the first image displayed on the display unit 3. In the fifth use example, the first image includes a distortion degree designation region for designating a permitted degree of distortion of shapes of polyhedra, unlike the third use example.

Here, the degree of distortion indicates a degree to which a shape of a polyhedron is distorted while using, as a reference, a shape of the polyhedron indicated by shape information, that is, a shape of the polyhedron displayed in the shape selection region. For example, the degree of distortion is decided on the basis of at least one of a position of a center of gravity of the polyhedron, a position of at least one vertex of the polyhedron, a length of at least one side of the polyhedron, an angle formed between at least two sides of the polyhedron, or an area of at least one face of the polyhedron while using the shape of the polyhedron indicated by the shape information as a reference.

For example, in a case where polyhedra having shapes indicated by the shape information are combined, the polyhedra cannot be arranged without any gaps in some cases. In such a case, the polyhedra can be arranged without any gaps by distorting a shape of at least one of the polyhedra. Therefore, in the fifth use example, the generation unit 12 attempts to generate a three-dimensional structure within a range of a degree of distortion permitted by a user.

The degree of distortion is, for example, expressed by the following formula (1) by using a Baur's method. In the formula (1), "D" represents a degree of distortion, "$l_i$" represents a distance from a center to an i-th vertex of a polyhedron, and "$l_{av}$" represents an average of distance from the center to vertexes of the polyhedron.

$$D = \frac{1}{n}\sum_{i=1}^{n}\frac{|l_i - l_{av}|}{l_{av}} \quad (1)$$

The degree of distortion is, for example, expressed by the following formula (2) by using a Robinson's method (quadratic elongation). In the formula (2), "λ" represents a degree of distortion, "$l_i$" represents a distance from a center to an i-th vertex of a polyhedron, and "$l_0$" represents a distance from a center to a vertex of a positive polyhedron having the same volume.

$$\lambda = \frac{1}{n}\sum_{i=1}^{n}\left(\frac{l_i}{l_0}\right)^2 \quad (2)$$

Figure 16A:
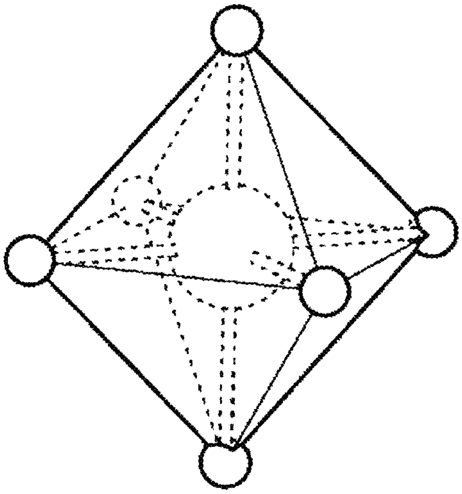
FIGS. 16A and 16B illustrate an example of a degree of distortion of a polyhedron.
Figure 16B:
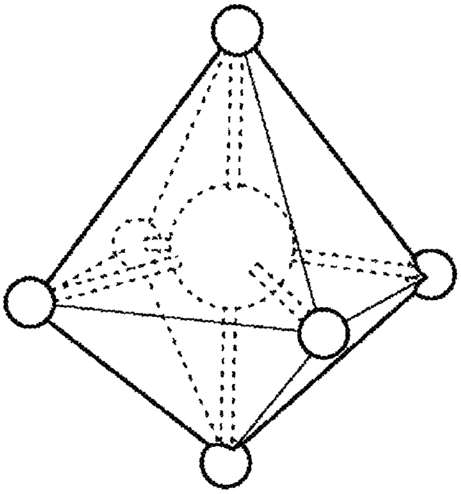
Figure 17:
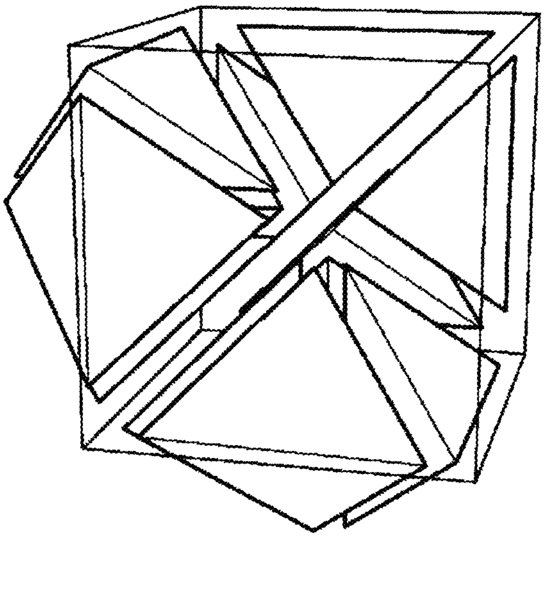
FIG. 17 illustrates an example of a three-dimensional structure having distortion.

FIGS. 16A and 16B illustrate an example of a degree of distortion of a polyhedron. FIG. 16A illustrates a shape of a polyhedron (a regular tetrahedron in this example) whose degree of distortion "D" is "0.0", that is, having no distortion. On the other hand, FIG. 16B illustrates a polyhedron (a shape of a regular tetrahedron in this example) whose degree of distortion "D" is "0.00869", that is, having distortion. FIG. 17 illustrates an example of a three-dimensional structure having distortion. FIG. 17 illustrates a three-dimensional structure (a bcc-type structure in this example) in which polyhedra having distortion (polyhedra obtained by distorting a regular tetrahedron) are arranged without any gaps.

In the distortion degree designation region, a textbox for designating a permitted degree of distortion of shapes of polyhedra is displayed. The user designates a permitted degree of distortion of shapes of polyhedra by inputting a desired degree of distortion in the textbox in the distortion degree designation region. Note that a desired range of degrees of distortion may be input in the textbox. As a result, the acquisition unit 11 (in the step of acquiring the first information) further acquires, as the first information, distortion degree information indicative of a permitted degree of distortion of shapes of polyhedra. In this case, when the user selects the execution icon, the generation unit 12 (in the step of generating the second information) generates second information concerning a three-dimensional structure in which at least one of polyhedra is distorted to a degree that does not exceed the degree of distortion indicated by the distortion degree information.

FIG. 15B illustrates an example of the second image displayed on the display unit 3. In the fifth use example, the second image further includes a column showing total distortion, which is a sum of distortion of a three-dimensional structure, in a table showing a list of three-dimensional structures generated by the generation unit 12, unlike the first use example.

Operation

Figure 18:
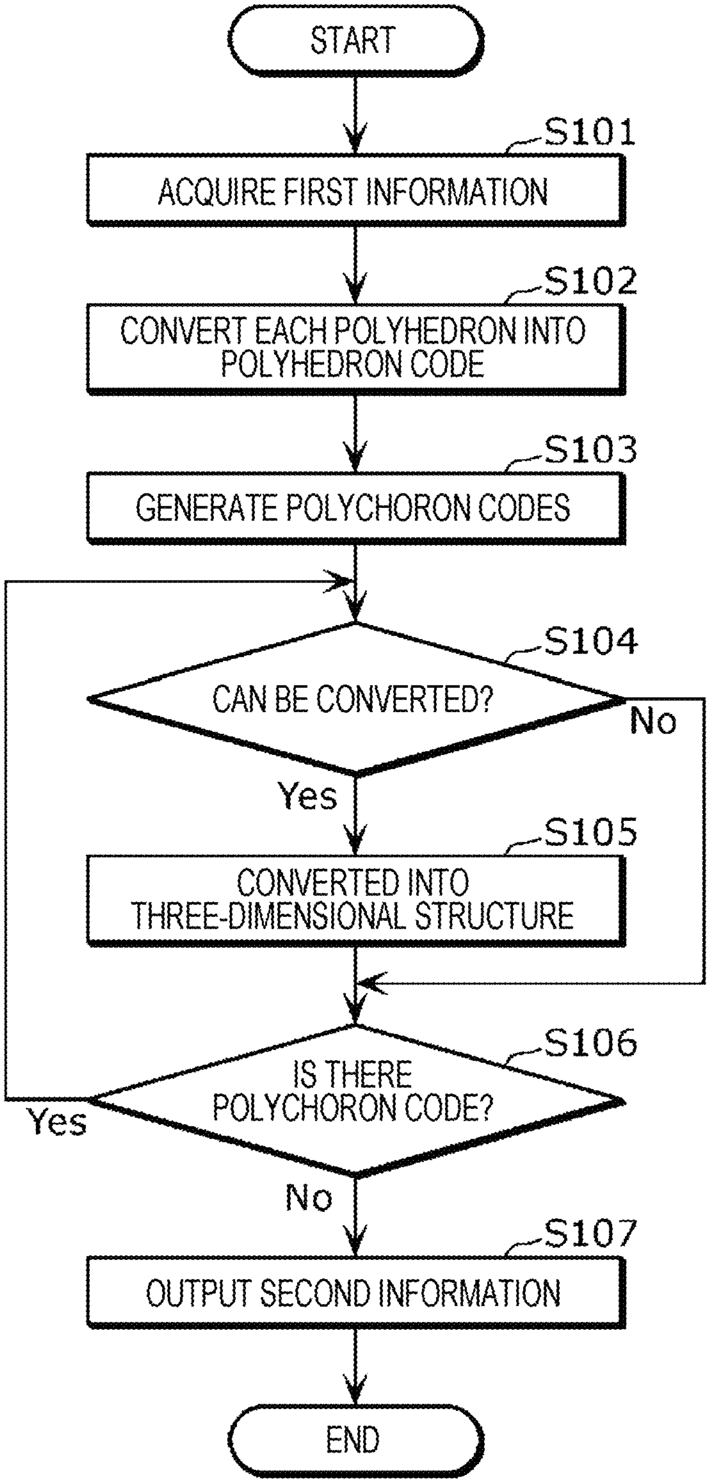
FIG. 18 is a flowchart illustrating an operation example of the information processing system according to Embodiment 1.

Operation of the information processing system 100 (i.e., the information processing method) according to Embodiment 1 is described below. FIG. 18 is a flowchart illustrating an operation example of the information processing system 100 according to Embodiment 1.

Step S101

The acquisition unit 11 acquires the first information. As described above, polyhedron data is read out from the first storage unit 4, and a user inputs (selects) the first information by using the input unit 2 while seeing the first image displayed on the display unit 3. In this way, the first information is acquired by the acquisition unit 11. Note that the user may input original data by using the input unit 2 without referring to the first image, and thereby the first information may be acquired by the acquisition unit 11.

Step S102

The generation unit 12 performs processing for converting the first information acquired by the acquisition unit 11 into first numerical sequences representing polyhedra. In this example, the generation unit 12 converts each polyhedron included in the first information into a polyhedron code.

Step S103

The generation unit 12 performs processing for generating a second numerical sequence representing a polychoron by using the first numerical sequences thus obtained. In this example, the generation unit 12 generates polychoron codes on the basis of the polyhedron codes obtained by the conversion.

Step S104

The generation unit 12 determines whether or not a generated polychoron code can be converted into a three-dimensional structure. The generation unit 12 can determine whether or not the polychoron code can be converted into a three-dimensional structure, for example, on the basis of whether or not faces of two polyhedra that are in contact with each other are identical and whether or not the polyhedra are arranged without any gaps (in other words, whether or not a filling rate is 100%). In a case where it is determined that the polychoron code can be converted (step S104: Yes), the generation unit 12 performs step S105. In a case where it is determined that the polychoron code cannot be converted (step S104: No) the generation unit 12 performs step S106.

Step S105

The generation unit 12 performs processing for converting the polychoron code into a three-dimensional structure. The conversion processing can be, for example, performed by using a method such as the method of K. Nishio et al. or the method of O. Delgado-Friedrichs et al. Next, the generation unit 12 performs step S106.

Step S106

The generation unit 12 determines whether or not there is a polychoron code that has not been determined yet as to whether or not it can be converted. In a case where there is a polychoron code that has not been determined yet (S106: Yes), the generation unit 12 returns to step S104. In a case where all polychoron codes have been determined (S106: No), the processing of the generation unit 12 is completed. Then, the information processing system 100 (the information processing method) performs step S107.

Step S107

The output unit 13 performs processing for outputting the second information generated by the generation unit 12. In this example, the output unit 13 outputs the second information by displaying the second image indicative of the second information generated by the generation unit 12 on the display unit 3.

The display unit 3 may include the display control unit 30. The display unit 3 including the display control unit 30 may be referred to as a display unit 3A. The output unit 13 may output the second information generated by the generation unit 12 to the display unit 3A. The display unit 3A may thus display the second information. That is, the output unit 13 may cause the second information to be displayed on the display unit 3A.

In a case where none of the polychoron codes can be converted into a three-dimensional structure by the generation unit 12, the second information is not generated. In a case where none of the polychoron codes can be converted into a three-dimensional structure by the generation unit 12, the second information is not displayed on the display unit 3.

Figure 19:
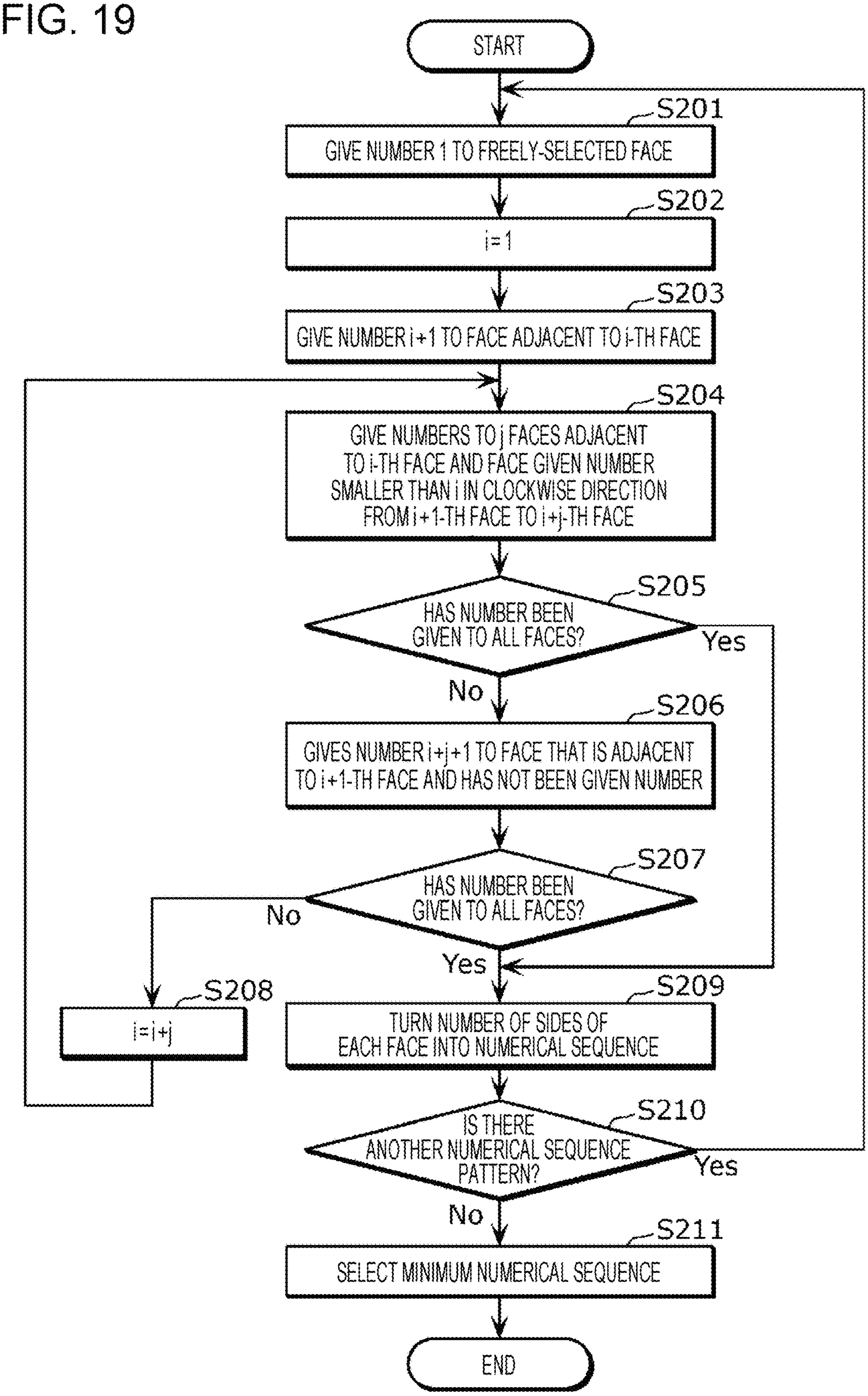
FIG. 19 is a flowchart illustrating an example of a process for generating a polyhedron code from a polyhedron.

Next, processing for converting a polyhedron into a polyhedron code is specifically described with reference to the drawings. FIG. 19 is a flowchart illustrating an example of a process for generating a polyhedron code from a polyhedron.

Step S201

The generation unit 12 gives a number "1" to a freely-selected face of a polyhedron.

Step S202

The generation unit 12 assigns "1" to a variable "i".

Step S203

The generation unit 12 gives a number "i+1" to a face adjacent to the "i"-th face.

Step S204

The generation unit 12 gives numbers to "j" (j is a variable) faces adjacent to the "i"-th face and a face given a number smaller than "i" in a clockwise direction from the "i+1"-th face to an "i+j"-th face. The number of faces adjacent to the "i"-th face and a face given a number smaller than "i" is assigned to the variable "j".

Step S205

The generation unit 12 determines whether or not a number has been given to all faces of the polyhedron. In a case where a number has been given to all faces of the polyhedron (step S205: Yes), the generation unit 12 performs step S209. In a case where not all faces of the polyhedron have been given a number (step S205: No), the generation unit 12 performs step S206.

Step S206

The generation unit 12 gives a number "i+j+1" to a face that is adjacent to the "i+1"th face and has not been given a number.

Step S207

The generation unit 12 determines whether or not a number has been given to all faces of the polyhedron. In a case where a number has been given to all faces of the polyhedron (step S207: Yes), the generation unit 12 performs step S209. In a case where not all faces of the polyhedron have been given a number (step S207: No), the generation unit 12 performs step S208.

Step S208

The generation unit 12 assigns "i+j" to the variable "i". Then, the generation unit 12 returns to step S204.

Step S209

The generation unit 12 turns the number of sides of each face into a numerical sequence by arranging the number of sides of each face in an order of the numbers given to all faces of the polyhedron.

Step S210

The generation unit 12 determines whether or not there is another numerical sequence pattern. In a case where there is another numerical sequence pattern (step S210: Yes), the generation unit 12 returns to step S201. In this case, the generation unit 12 gives a number "1" to a freely-selected face different from the face given the number "1" in the past in step S201. In a case where there is no other numerical sequence pattern (step S210: No), the generation unit 12 performs step S211.

Step S211

The generation unit 12 selects a minimum numerical sequence from among one or more numerical sequences. The selected numerical sequence becomes a polyhedron code.

A specific example of processing for converting a polyhedron into a polyhedron code is described below.

Figure 20:
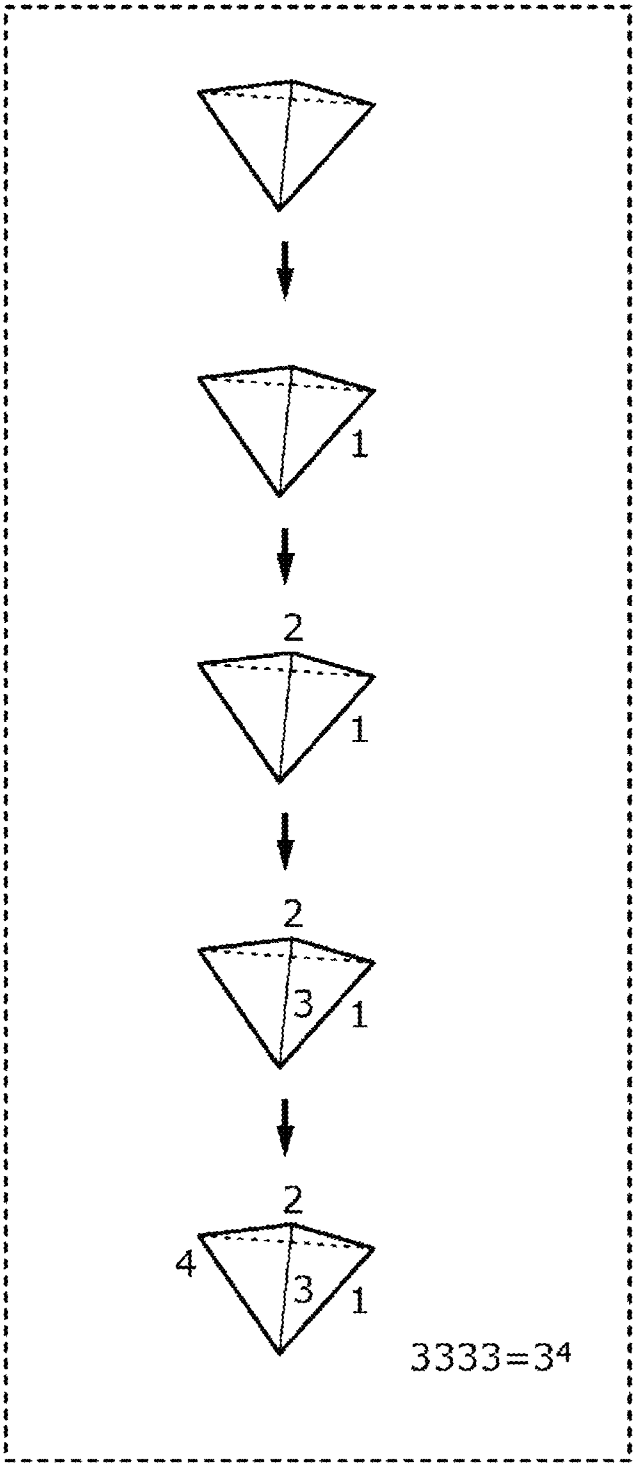
FIG. 20 illustrates an example of a process for generating a polyhedron code from a regular tetrahedron.

FIG. 20 illustrates an example of a process for generating a polyhedron code from a regular tetrahedron. First, the generation unit 12 gives a number "1" to a freely-selected face. Then, the generation unit 12 sequentially gives numbers "2", "3", and "4" to faces adjacent to the face "1" in a clockwise direction (left-handed system).

Figure 38:
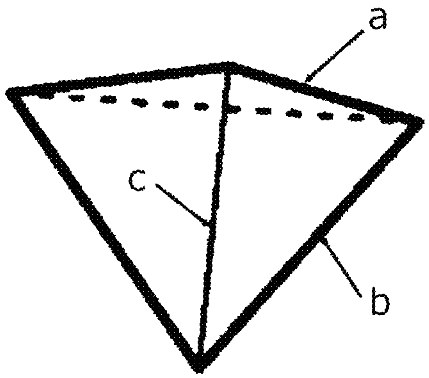
FIG. 38 illustrates a side a, a side b, and a side c of a $face_1$ of a regular tetrahedron.
Figure 39:
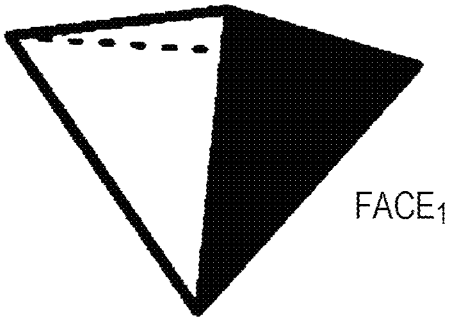
FIG. 39 illustrates a $face_1$ of a regular tetrahedron.

In FIG. 20, a face given the number "1" is referred to as a $face_1$, a face given the number "2" is referred to as a $face_2$, a face given the number "3" is referred to as a $face_3$, and a face given the number "4" is referred to as a $face_4$. The $face_1$ is a near-side face on the right of each regular tetrahedron illustrated in FIG. 20. Three sides of the $face_1$ are referred to as a side a, a side b, and a side c in a clockwise direction. FIG. 38 illustrates the side a, the side b, and the side c of the $face_1$ of the regular tetrahedron. FIG. 39 illustrates the $face_1$ of the regular tetrahedron. In FIG. 39, the $face_1$ is blacked out. The $face_2$ shares the side a with the $face_1$, the $face_3$ shares the side b with the $face_1$, and the $face_4$ shares the side c with the $face_1$.

In this way, all the faces are given numbers, and therefore the generation unit 12 generates a numerical sequence by using the number of sides of faces as terms in an order of the numbers. Specifically, in a case where a face is a triangle, the face has three sides, and therefore a term corresponding to the face is "3". Accordingly, a numerical sequence representing faces of a regular tetrahedron is "$3333=3^4$" in an order from the number "1" to the number "4". In this case, there is no other numerical sequence pattern, and therefore the regular tetrahedron is converted into a polyhedron code "$3^4$".

Figure 21:
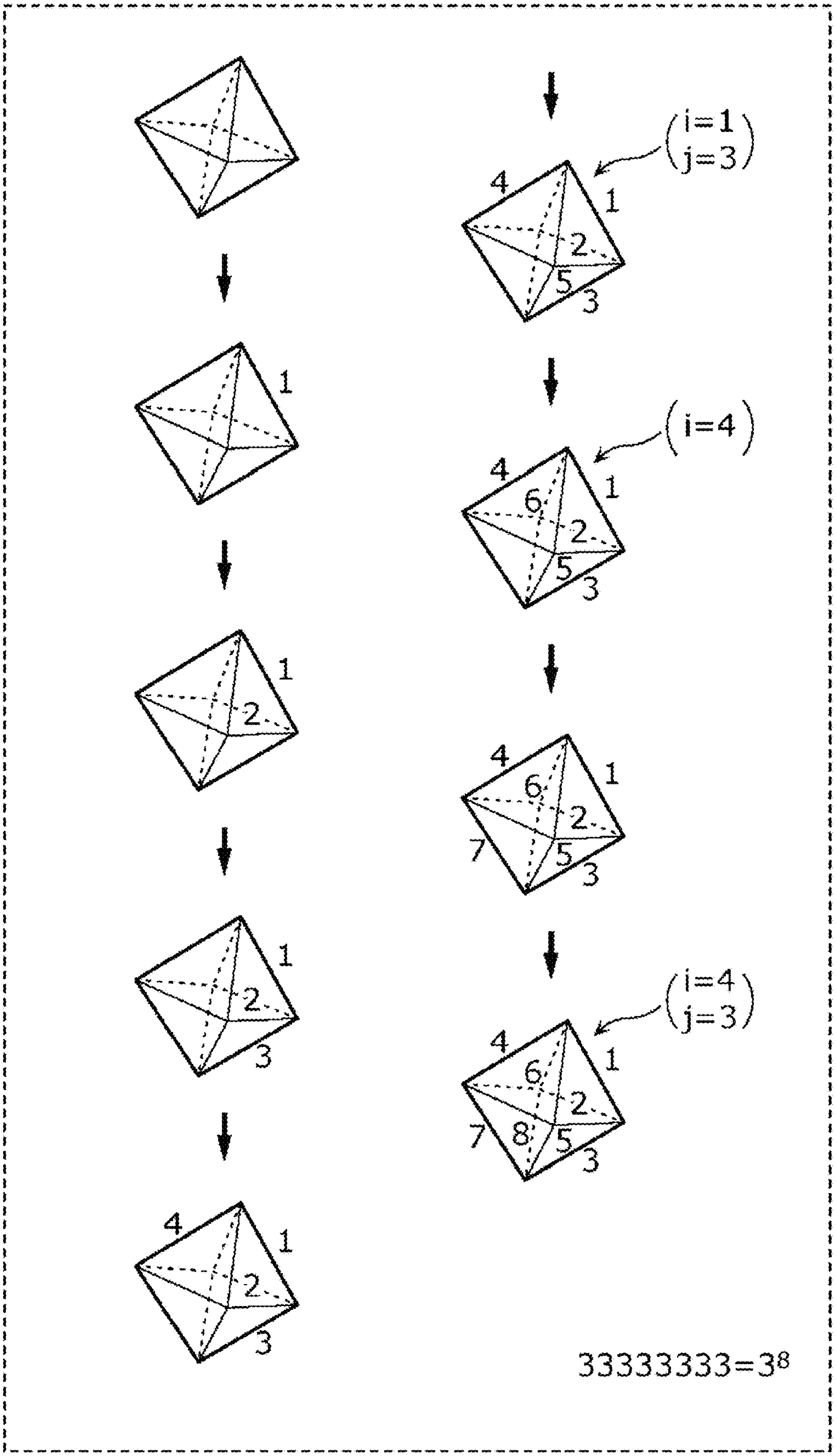
FIG. 21 illustrates an example of a process for generating a polyhedron code from a regular octahedron.

FIG. 21 illustrates an example of a process for generating a polyhedron code from a regular octahedron. First, the generation unit 12 gives a number "1" to a freely-selected face. Then, the generation unit 12 sequentially gives numbers "2", "3", and "4" to faces adjacent to the face "1" in a clockwise direction (left-handed system). Next, the generation unit 12 gives a number "5" to a face that is adjacent to the face "2" and has not been given a number yet. Then, the generation unit 12 sequentially gives numbers "6" and "7" to faces adjacent to the faces given the number "4" and smaller numbers in a clockwise direction (left-handed system) from the face "5". Furthermore, the generation unit 12 gives a number "8" to a face that is adjacent to the face "5" and has not been given a number yet.

Figure 40:
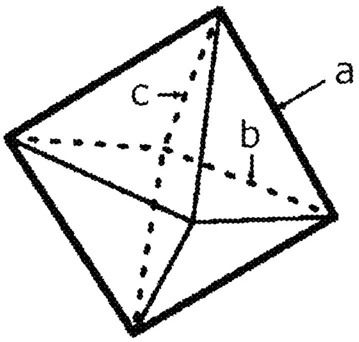
FIG. 40 illustrates a side a, a side b, and a side c of a $face_1$ of a regular octahedron.
Figure 41:
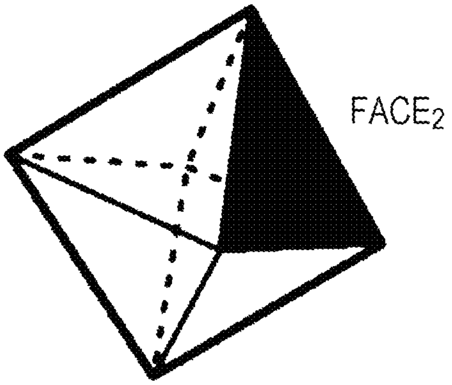
FIG. 41 illustrates a $face_2$ of a regular octahedron.
Figure 42:
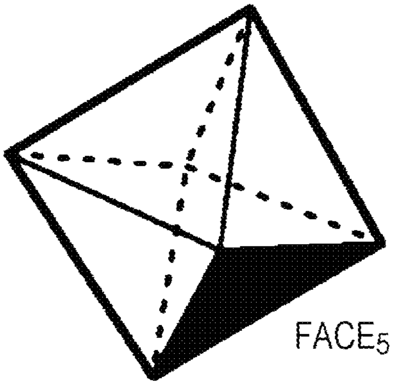
FIG. 42 illustrates a $face_5$ of a regular octahedron.
Figure 43:
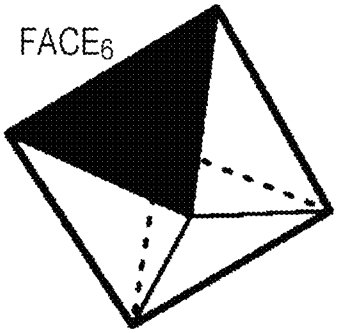
FIG. 43 illustrates a $face_6$ of a regular octahedron.

In FIG. 21, the face given the number "1" is referred to as a $face_1$, . . . , and the face given the number "8" is referred to as a $face_8$. The $face_1$ is a far-side face on the right of each regular octahedron illustrated in FIG. 21. Three sides of the $face_1$ are referred to as a, b, and c in a clockwise direction. FIG. 40 illustrates the side a, the side b, and the side c of the $face_1$ of the regular octahedron. The $face_2$ shares the side a with the $face_1$, the $face_3$ shares the side b with the $face_1$, and the $face_4$ shares the side c with the $face_1$. FIG. 41 illustrates the $face_2$ of the regular octahedron. In FIG. 41, the $face_2$ is blacked out. FIG. 42 illustrates the $face_5$ of the regular octahedron. In FIG. 42, the $face_5$ is blacked out. FIG. 43 illustrates the $face_6$ of the regular octahedron. In FIG. 43, the $face_6$ is blacked out.

In this way, all the faces are given numbers, and therefore the generation unit 12 generates a numerical sequence by using the number of sides of faces as terms in an order of the numbers. Specifically, in a case where a face is a triangle, the face has three sides, and therefore a term corresponding to the face is "3". Accordingly, a numerical sequence representing faces of a regular octahedron is "$33333333=3^8$" in an order from the number "1" to the number "8". In this case, there is no other numerical sequence pattern, the regular octahedron is converted into a polyhedron code "$3^8$".

Figure 22:
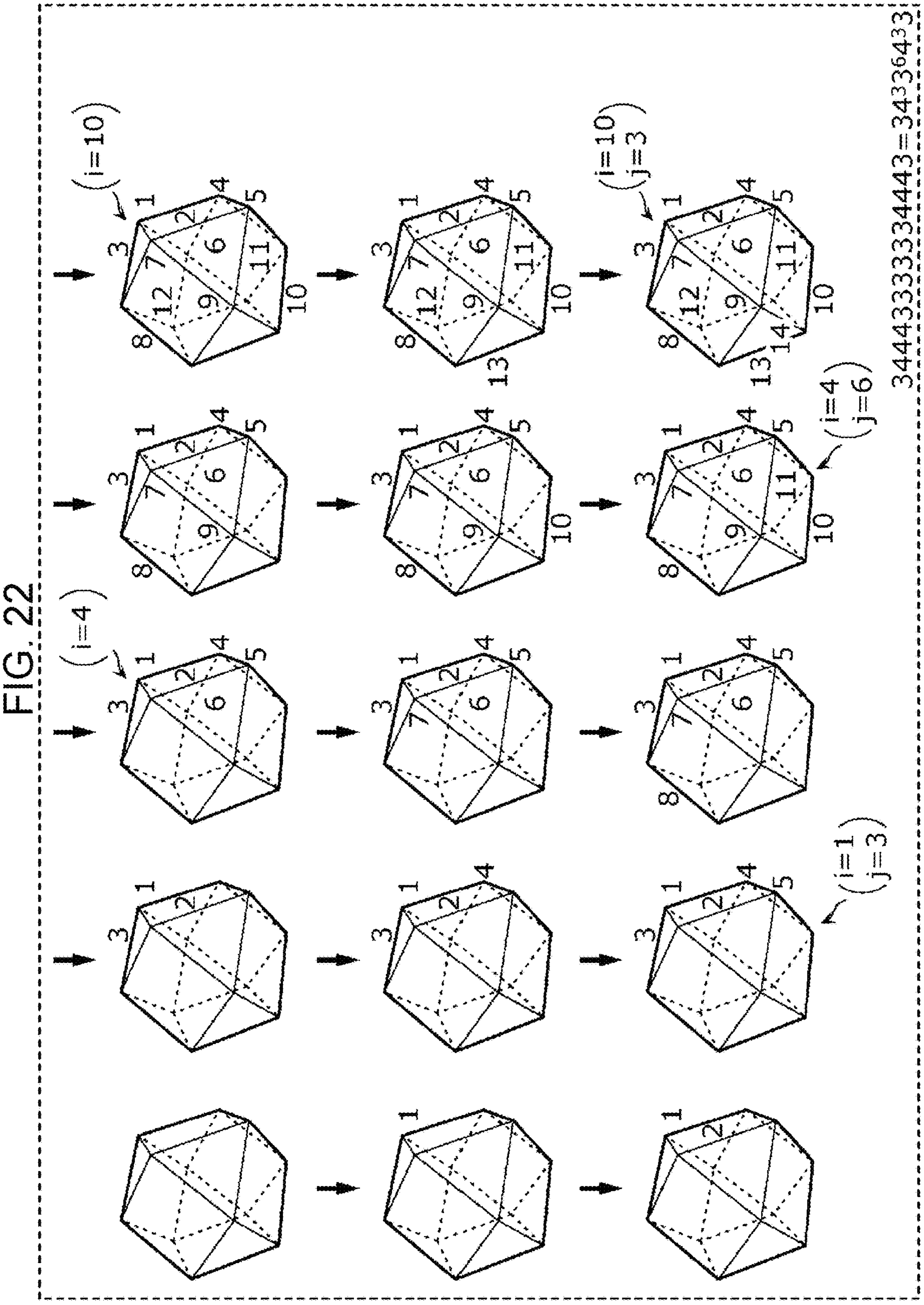
FIG. 22 illustrates an example of a process for generating a polyhedron code from a cuboctahedron.

FIG. 22 illustrates an example of a process for generating a polyhedron code from a cuboctahedron. First, the generation unit 12 gives a number "1" to a freely-selected face. Then, the generation unit 12 sequentially gives numbers "2", "3", and "4" to faces adjacent to the face "1" in a clockwise direction (left-handed system). Next, the generation unit 12 gives a number "5" to a face that is adjacent to the face "2" and has not been given a number yet. Then, the generation unit 12 sequentially gives numbers "6", "7", "8", "9", and "10" to faces adjacent to the faces given the number "4" and smaller numbers in a clockwise direction (left-handed system) from the face "5". Furthermore, the generation unit 12 gives a number "11" to a face that is adjacent to the face "5" and has not been given a number yet. Then, the generation unit 12 sequentially gives numbers "12" and "13" to faces adjacent to the faces given the number "10" and smaller numbers in a clockwise direction (left-handed system) from the face "11". Furthermore, the generation unit 12 gives a number "14" to a face that is adjacent to the face "11" and has not been given a number yet.

Figure 44:
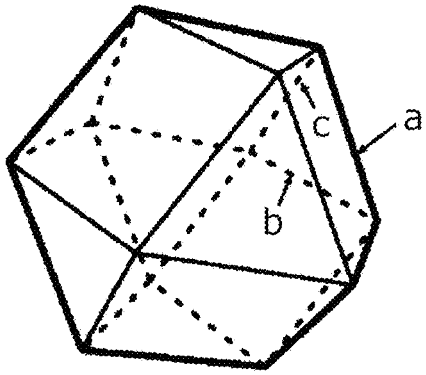
FIG. 44 illustrates a side a, a side b, and a side c of a $face_1$ of a cuboctahedron.
Figure 45:
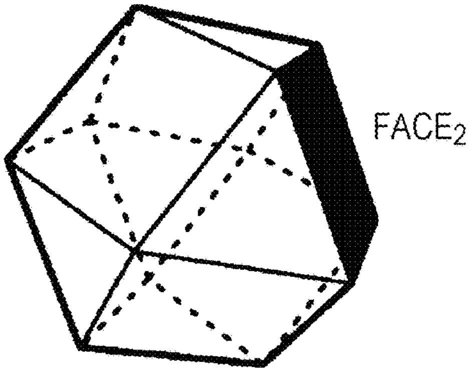
FIG. 45 illustrates a $face_2$ of a cuboctahedron.
Figure 46:
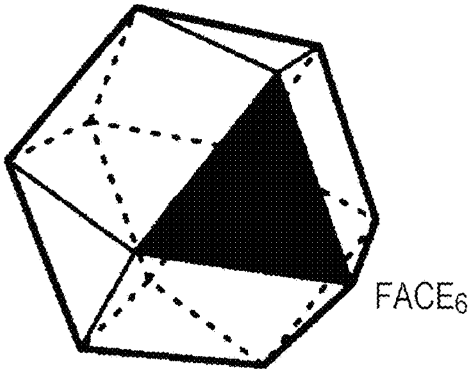
FIG. 46 illustrates a $face_6$ of a cuboctahedron.
Figure 47:
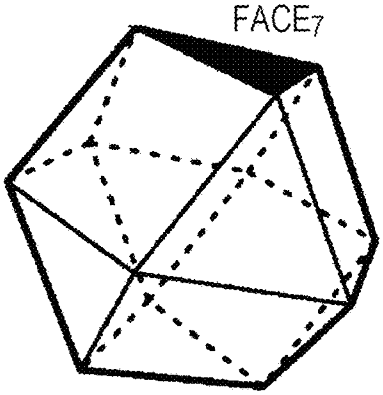
FIG. 47 illustrates a $face_7$ of a cuboctahedron.

In FIG. 22, the face given the number "1" is referred to as a $face_1$, . . . , and the face given the number "14" is referred to as a $face_{14}$. The $face_1$ is a far-side triangular face on the right of each cuboctahedron illustrated in FIG. 22. Three sides of the $face_1$ are referred to as a, b, and c in a clockwise direction. FIG. 44 illustrates the side a, the side b, and the side c of the $face_1$ of the cuboctahedron. The $face_2$ shares the side a with the $face_1$, the $face_3$ shares the side b with the $face_1$, and the $face_4$ shares the side c with the $face_1$. FIG. 45 illustrates the $face_2$ of the cuboctahedron. In FIG. 45, the $face_2$ is blacked out. FIG. 46 illustrates the $face_6$ of the cuboctahedron. In FIG. 46, the $face_6$ is blacked out. FIG. 47 illustrates the $face_7$ of the cuboctahedron. In FIG. 47, the $face_7$ is blacked out.

In this way, all the faces are given numbers, and therefore the generation unit 12 generates a numerical sequence by using the number of sides of faces as terms in an order of the numbers. Specifically, in a case where a face is a triangle, the face has three sides, and therefore a term corresponding to the face is "3". In a case where a face is a quadrangular, the face has four sides, and therefore a term corresponding to the face is "4". Accordingly, a numerical sequence representing faces of the cuboctahedron is "$34443333334443=34^33^64^33$" in an order from the number "1" to the number "14". In this case, this numerical sequence is a minimum numerical sequence smaller than other numerical sequence patterns, and therefore the cuboctahedron is converted into a polyhedron code "$34^33^64^33$".

In a case where an integer A is smaller than an integer B, a numerical sequence A is smaller than a numerical sequence B. In the above example of the cuboctahedron, a numerical sequence "$34443333334443=34^33^64^33$" is obtained in a case where a triangle is first selected, but a numerical sequence "$43333444433334=43^44^43^44$" is obtained in a case where a quadrangle is selected. That is, since a single polyhedron has numerical sequences, it is necessary to uniquely decide a numerical sequence. In one example, a minimum numerical sequence may be selected. In this case, since the numerical sequence 43333444433334 is larger than the numerical sequence 34443333334443, the numerical sequence 34443333334443 is selected.

Figure 23:
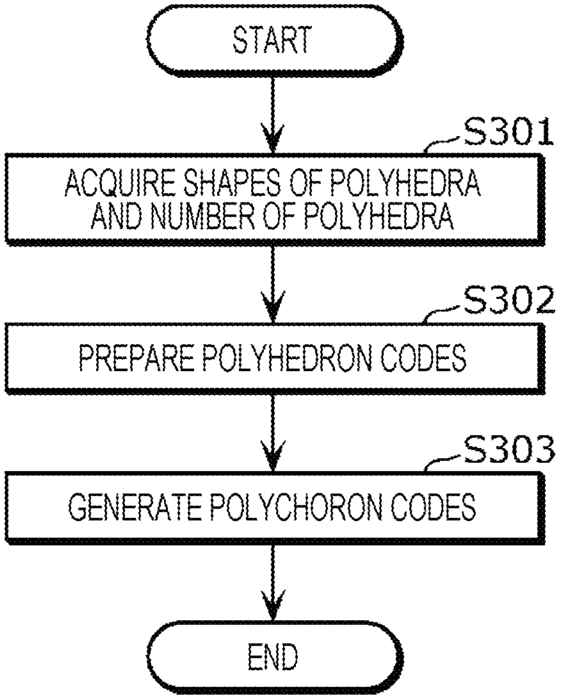
FIG. 23 is a flowchart illustrating an example of a process for generating polychoron codes from polyhedron codes.

Processing for generating polychoron codes on the basis of polyhedron codes is specifically described below with reference to the drawings. FIG. 23 is a flowchart illustrating an example of a process for generating polychoron codes from polyhedron codes. In this example, it is assumed that the acquisition unit 11 acquires, as the first information, shapes of polyhedra and the number of polyhedra for each shape.

Step S301

The generation unit 12 acquires shapes of polyhedra and the number of polyhedra for each shape that are included in the first information acquired by the acquisition unit 11.

Step S302

The generation unit 12 prepares polyhedron codes by converting each of the polyhedra into a polyhedron code.

Step S303

The generation unit 12 generates polychoron codes on the basis of the polyhedron codes.

For example, assume that the polyhedra include eight regular tetrahedra and four regular octahedra. In this case, a polyhedron code "$3^4$" corresponding to a regular tetrahedron is expressed as "T=$3^4$", and a polyhedron code "$3^8$" corresponding to a regular octahedron is expressed as "O=$3^8$". Accordingly, in step S303, the generation unit 12 generates polychoron codes by rearranging a numerical sequence "OOOOTTTTTTTT" of the polyhedron codes. For example, a polychoron code is "TOOOOTTTTTTT=$TO^4T^7$". That is, in step S303, polychoron codes are generated on the basis of the polyhedron codes, that is, eight Ts and four Os. Each of the polychoron codes includes eight Ts and four Os. "OOOOTTTTTTTT" and "TOOOOTTTTTTT" are different polychoron codes.

Figure 24:
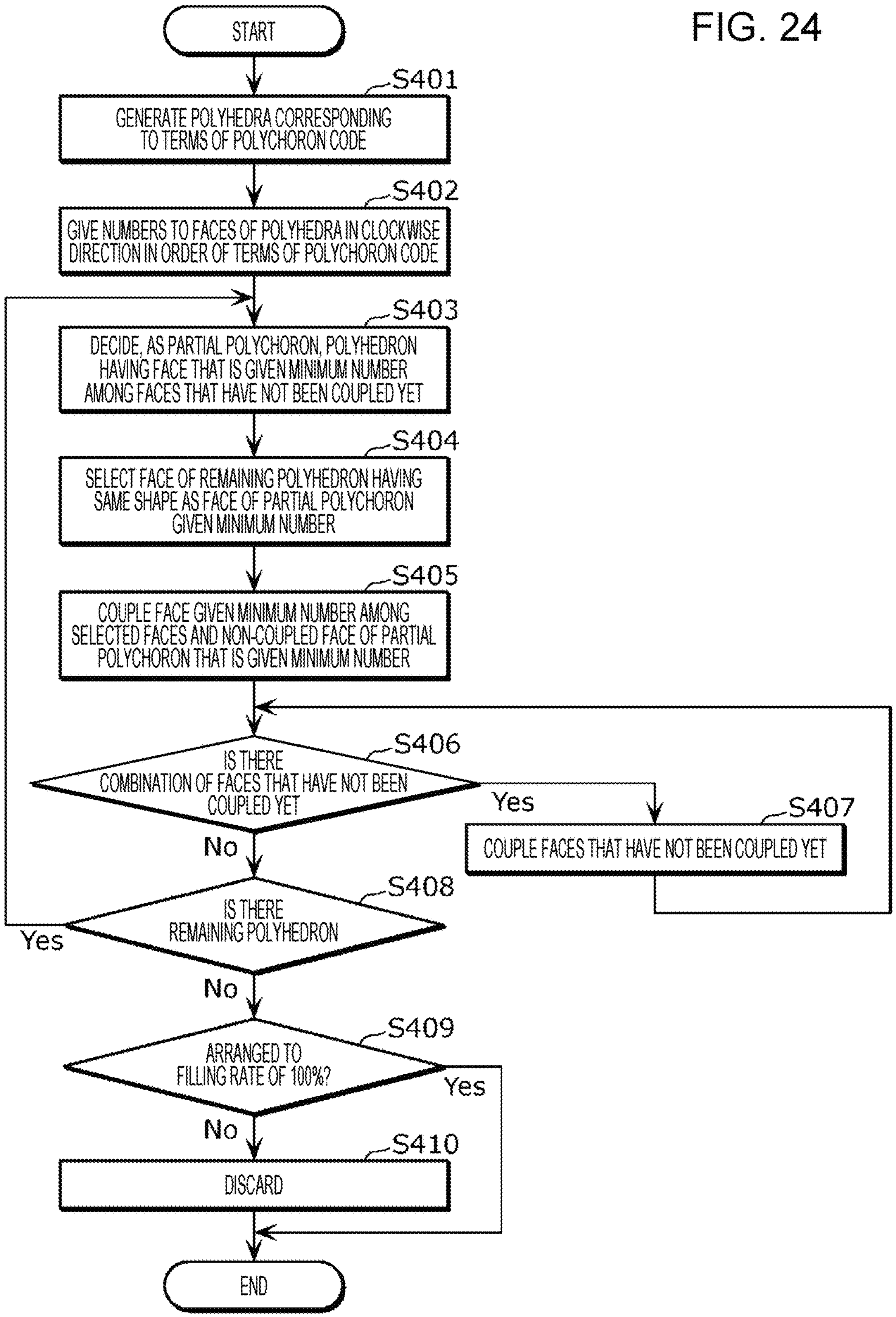
FIG. 24 is a flowchart illustrating an example of a process for generating a three-dimensional structure from a polychoron code.

Processing for converting a polychoron code into a three-dimensional structure is specifically described below with reference to the drawings. The processing described below includes processing for determining whether or not a polychoron code can be converted into a three-dimensional structure. FIG. 24 is a flowchart illustrating an example of a process for generating a three-dimensional structure from a polychoron code.

Step S401

The generation unit 12 generates terms of a polychoron code, that is, polyhedra corresponding to polyhedron codes.

Step S402

The generation unit 12 gives numbers to faces of the polyhedra in a clockwise direction in an order of the terms of the polychoron code. For example, in a case where numbers "1" to "4" are given to a polyhedron corresponding to the first term of the polychoron code, numbers starting from a number "5" are given to a polyhedron corresponding to the second term of the polychoron code. That is, the generation unit 12 gives numbers to faces of each polyhedron so that the polyhedra do not have the same number.

Step S403

The generation unit 12 decides, as a partial polychoron, a polyhedron having a face that is given a minimum number among faces that have not been coupled yet.

Step S404

The generation unit 12 selects a face of a remaining polyhedron having the same shape as the face of the partial polychoron given the minimum number. For example, in a case where the shape of the face of the partial polychoron given the minimum number is triangular, a face of the same triangular shape is selected from among faces of remaining polyhedra. Here, one face may be selected or faces may be selected.

Step S405

The generation unit 12 couples a face given a minimum number among the selected faces and the non-coupled face of the partial polychoron that is given a minimum number.

Step S406

The generation unit 12 determines whether or not the faces of the partial polychoron and selected faces of remaining polyhedra include a combination of faces that have not been coupled yet. In a case where there is a combination of faces that have not been coupled yet (step S406: Yes), the generation unit 12 performs step S407. In a case where there is no combination of faces that have not been coupled yet (step S406: No), the generation unit 12 performs step S408.

Step S407

The generation unit 12 couples faces that have not been coupled yet among the faces of the partial polychoron and the selected faces of the remaining polyhedra. Then, the generation unit 12 returns to step S406.

Step S408

The generation unit 12 determines whether or not there is a remaining polyhedron that has not been coupled yet. In a case where there is a remaining polyhedron that has not been coupled yet (step S408: Yes), the generation unit 12 returns to step S403. In a case where there is no remaining polyhedron that has not been coupled yet (step S408: No), the generation unit 12 performs step S409.

Step S409

The generation unit 12 determines whether or not all the polyhedra have been arranged to a filling rate of 100%, in other words, whether or not all the polyhedra have been arranged without any gaps. In a case where all polyhedra have been arranged to a filling rate of 100% (step S409: Yes), the processing of the generation unit 12 is completed. This means that the generation unit 12 has successfully converted the polychoron code into a three-dimensional structure. In a case where the filling rate is not 100% (step S409: No), the generation unit 12 performs step S410.

Step S410

The generation unit 12 discards a three-dimensional structure whose filling rate is not 100% and completes the processing. In this case, the generation unit 12 does not convert the polychoron code into a three-dimensional structure.

Figure 25:
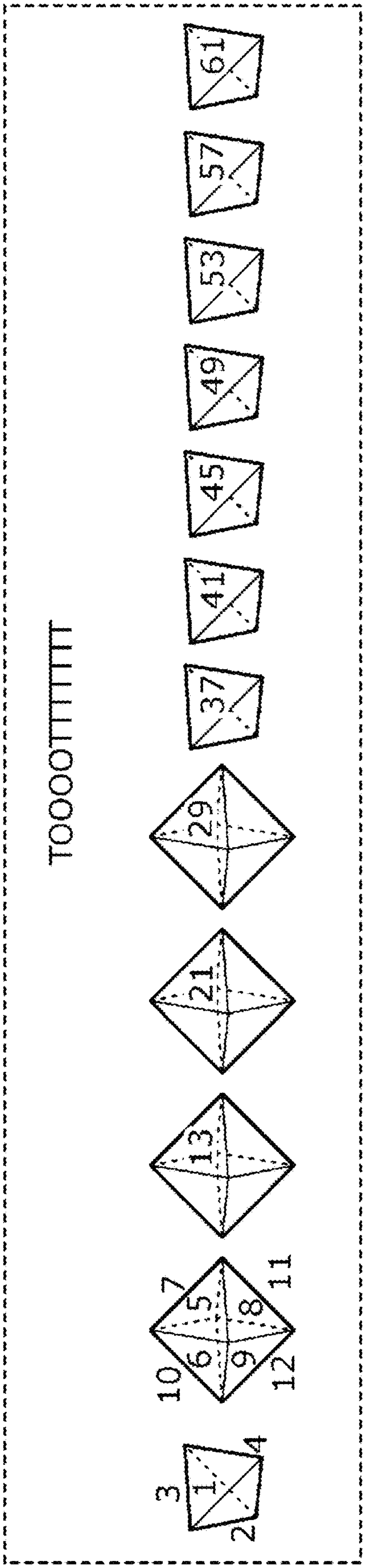
FIG. 25 illustrates a specific example of a polychoron code.
Figure 26:
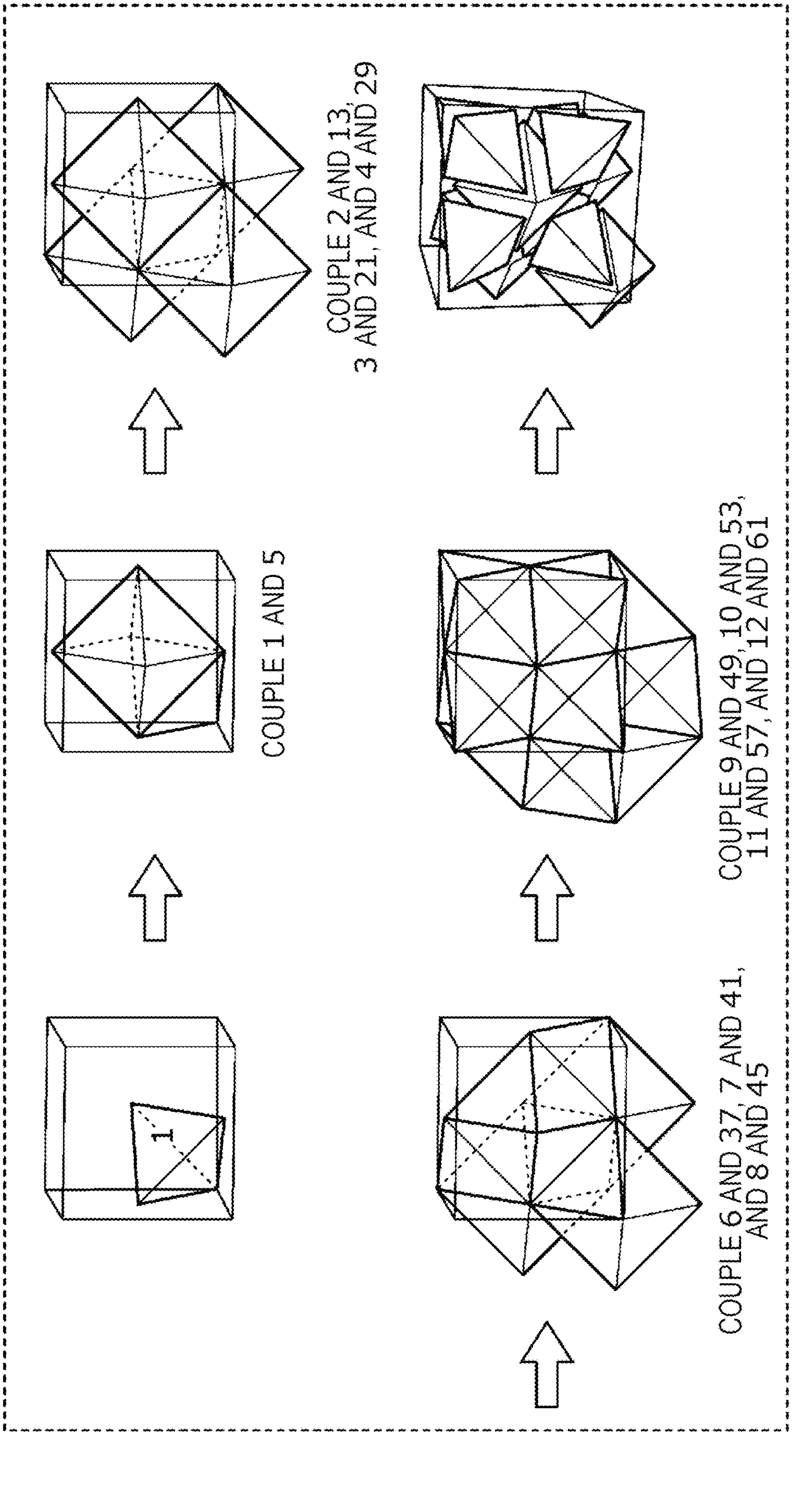
FIG. 26 illustrates a specific example of a process for generating a three-dimensional structure from a polychoron code.

A specific example of the processing for converting a polyhedron code into a three-dimensional structure is described below with reference to the drawings. FIG. 25 illustrates a specific example of a polychoron code. FIG. 26 illustrates a specific example of a process for generating a three-dimensional structure from a polychoron code. As illustrated in FIG. 25, the following describes a case where a polychoron code "TOOOOTTTTTTT" is converted into a three-dimensional structure.

First, the generation unit 12 converts polyhedron codes "T" and "O" in the polychoron code into corresponding polyhedra. In this case, the polyhedron code "T" is a regular tetrahedron, and the polyhedron code "O" is a regular octahedron. Next, the generation unit 12 gives numbers to faces of the polyhedra in a clockwise direction in an order of terms included in the polychoron code. For example, numbers "1" to "4" are given to faces of a regular tetrahedron corresponding to the first term (leftmost term) of the polychoron code, and numbers "5" to "10" are given to faces of a regular octahedron corresponding to the second term. Then, the generation unit 12 decides, as a partial polychoron, the regular tetrahedron corresponding to the first term of the polychoron code.

Next, the generation unit 12 selects faces of remaining polyhedra having a shape of a face given a minimum number among faces of the regular tetrahedron that is the partial polychoron. In this example, a face "1" of the partial polychoron, which is a face given a minimum number, has a triangular shape, and faces of all remaining polyhedra have a triangular shape, and therefore the faces of all remaining polyhedra are selected. Then, the generation unit 12 couples a face given a minimum number among the selected faces and the non-coupled face of the partial polychoron that is given a minimum number. In this example, the face "1" of the regular tetrahedron that is the partial polychoron and a face "5" of the regular octahedron corresponding to the second term of the polychoron code are coupled.

Next, the generation unit 12 repeats the processing of coupling faces that have not been coupled yet since the faces of the partial polychoron and selected faces of the remaining polyhedra include a combination of faces that have not been coupled yet. In this example, the generation unit 12 couples a face "2", which is a non-coupled face of the partial polychoron given a minimum number, and a face "13", which is a non-coupled face given a minimum number among the selected faces of the remaining polyhedra. Similarly, the generation unit 12 couples a face "3" and a face "21" and couples a face "4" and a face "29".

Next, since there is a remaining polyhedron that has not been coupled yet, the generation unit 12 decides, as a new partial polychoron, a polyhedron (in this example, the regular octahedron corresponding to the second term of the polychoron code) having a non-coupled face given a minimum number among the remaining polyhedra and repeats processing similar to that described above.

Then, the generation unit 12 generates a three-dimensional structure whose filling rate is 100% by repeating the above processing until there is no remaining polyhedron that has not been coupled yet. Specifically, the generation unit 12 couples a face "6", which is a non-coupled face of the new partial polychoron that is given a minimum number, and a face "37", which is a non-coupled face that is given a minimum number among selected faces of the remaining polyhedra. Similarly, the generation unit 12 couples a face "7" and a face "41", couples a face "8" and a face "45", couples a face "9" and a face "49", couples a face "10" and a face "53", couples a face "11" and a face "57", and couples a face "12" and a face "59". In the case of the polychoron code "TOOOTTTTTTT", the three-dimensional structure generated by the generation unit 12 is a fcc-type structure.

Figure 27:
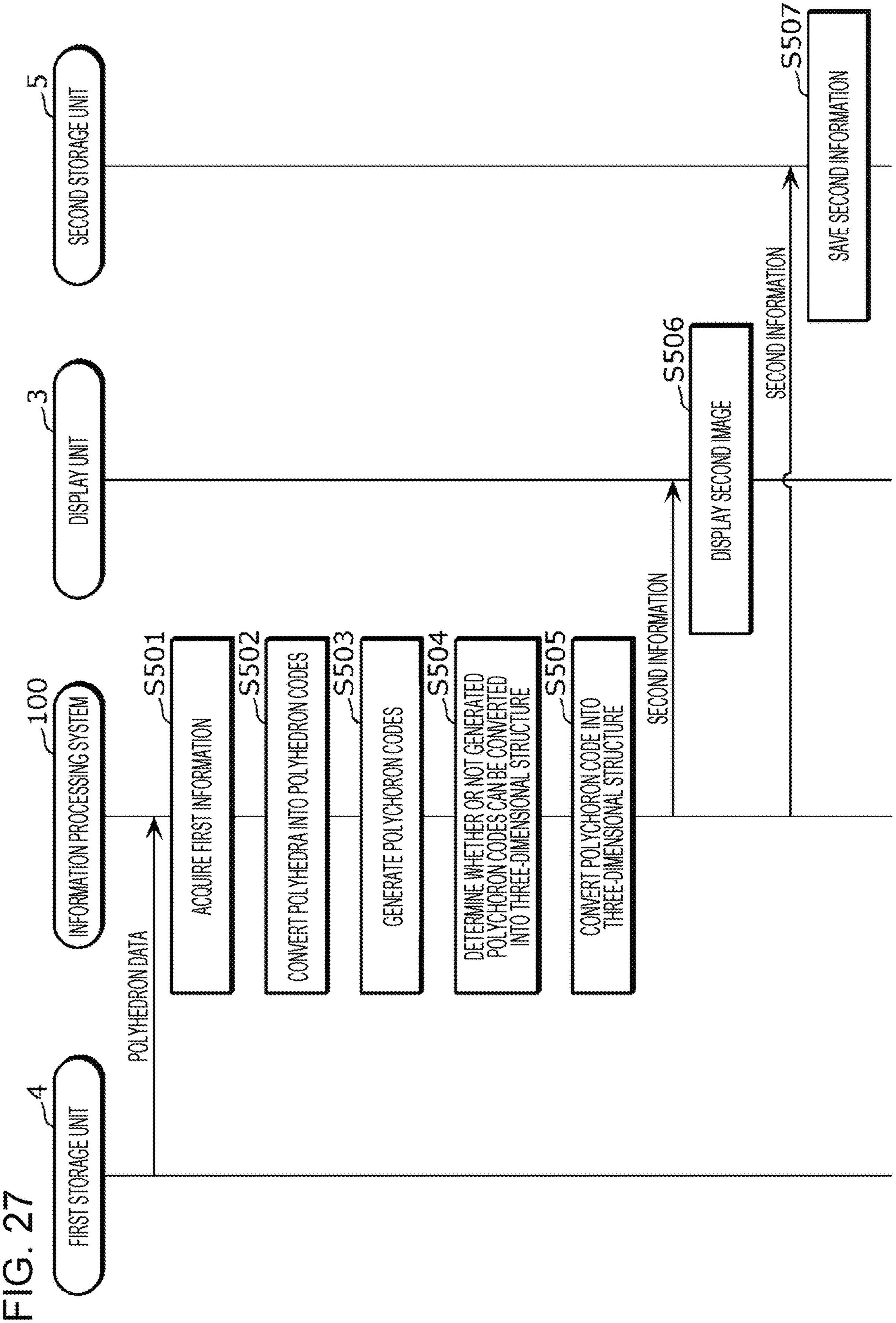
FIG. 27 is a sequence diagram illustrating an operation example of the information processing system and the display unit, the first storage unit, and the second storage unit according to Embodiment 1.

An operation example of the information processing system 100 and the display unit 3, the first storage unit 4, and the second storage unit 5 according to Embodiment 1 is described below with reference to the drawings. FIG. 27 is a sequence diagram illustrating an operation example of the information processing system 100 and the display unit 3, the first storage unit 4, and the second storage unit 5 according to Embodiment 1.

Step S501

The acquisition unit 11 of the information processing system 100 acquires the first information. In this example, polyhedron data stored in the first storage unit 4 is read out, and a user inputs (selects) the first information by using the input unit 2 while seeing the first image displayed on the display unit 3. In this way, the first information is acquired by the acquisition unit 11.

Step S502

The generation unit 12 of the information processing system 100 performs processing for converting polyhedra included in the first information acquired by the acquisition unit 11 into polyhedron codes.

Step S503

The generation unit 12 of the information processing system 100 performs processing for generating polychoron codes on the basis of the polyhedron codes obtained by the conversion.

Step S504

The generation unit 12 of the information processing system 100 performs processing for determining whether or not the generated polychoron codes can be converted into a three-dimensional structure.

Step S505

The generation unit 12 of the information processing system 100 performs processing for converting a polychoron code determined as being convertible into a three-dimensional structure.

Step S506

The display unit 3 displays the second image indicative of the second information output from the output unit 13 of the information processing system 100.

Step S507

When the user selects a three-dimensional structure to be saved while seeing the second image displayed on the display unit 3, the information processing system 100 gives the second information concerning the selected three-dimensional structure to the second storage unit 5. In this way, the second storage unit 5 stores therein the second information concerning the three-dimensional structure selected by the user.

As described above, in Embodiment 1, by inputting information on polyhedra, a three-dimensional structure (i.e., a space-filled structure in a three-dimensional space) made up of a combination of the input polyhedra can be exhaustively generated. Accordingly, in Embodiment 1, an unknown material can be searched for by using the three-dimensional structure exhaustively generated, and therefore an unknown material can be searched for efficiently.

Although the information processing system 100 (information processing method) according to Embodiment 1 converts polyhedra into polyhedron codes, generates polychoron codes from the polyhedron codes thus obtained by the conversion, and converts the generated polychoron codes into a three-dimensional structure, this is not restrictive. The information processing system 100 according to Embodiment 1 may convert polyhedra into polyhedron graphs, generate periodic graphs from the polyhedron graphs thus obtained by the conversion, and convert the generated periodic graphs into a three-dimensional structure. That is, the generation unit 12 (the step of generating the second information) may perform processing for converting the acquired first information into polyhedron graphs representing the polyhedra and processing for converting periodic graphs generated by the polyhedron graphs thus obtained by the conversion into a three-dimensional structure.

Figure 28:
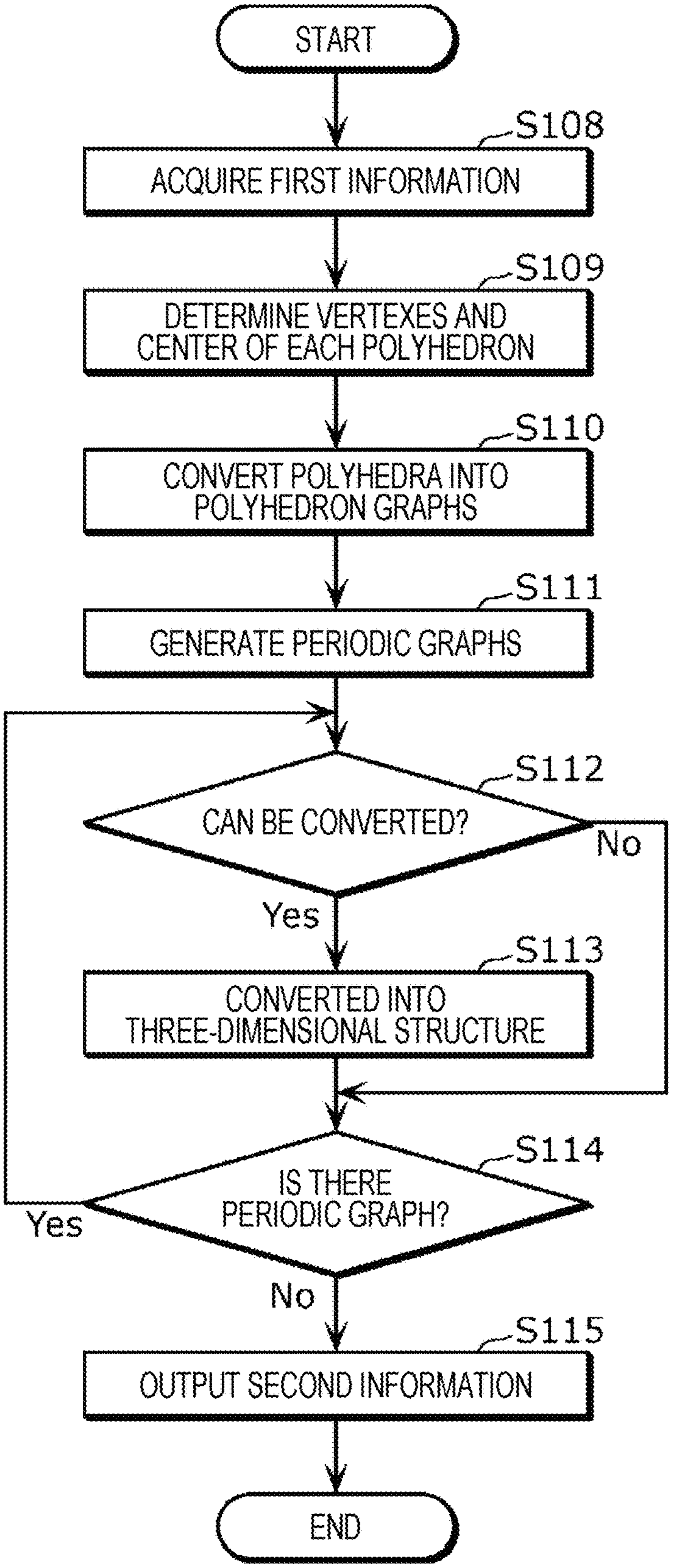
FIG. 28 is a flowchart illustrating another operation example of the information processing system according to Embodiment 1.

The above operation of the information processing system 100 (i.e., the information processing method) according to Embodiment 1 is described below. FIG. 28 is a flowchart illustrating another operation example of the information processing system 100 according to Embodiment 1.

Step S108

The acquisition unit 11 acquires the first information. As described above, polyhedron data stored in the first storage unit 4 is read out, and a user inputs (selects) the first information by using the input unit 2 while seeing the first image displayed on the display unit 3. In this way, the first information is acquired by the acquisition unit 11. Note that the user may input original data by using the input unit 2 without referring to the first image, and thereby the first information may be acquired by the acquisition unit 11.

Step S109

The generation unit 12 determines positions of vertexes (vertex sites) of each polyhedron and a position of a center (center site) of each polyhedron on the basis of the acquired first information.

Step S110

The generation unit 12 performs processing for converting the first information acquired by the acquisition unit 11 into polyhedron graphs representing polyhedra. In this example, the generation unit 12 converts each polyhedron included in the first information into a polyhedron graph.

Step S111

The generation unit 12 performs processing for generating periodic graphs by using the polyhedron graphs thus obtained by the conversion. In this example, the generation unit 12 generates periodic graphs on the basis of a combination of the polyhedron graphs obtained by the conversion.

Step S112

The generation unit 12 determines whether or not the periodic graphs thus generated can be converted into a three-dimensional structure. The generation unit 12 can determine whether or not a periodic graph can be converted into a three-dimensional structure, for example, on the basis of whether or not faces of two polyhedra that are in contact with each other are identical and whether or not polyhedra are arranged without any gaps (in other words, whether or not a filling rate is 100%). In a case where it is determined that the periodic graph can be converted (step S112: Yes), the generation unit 12 performs step S113. In a case where the periodic graph cannot be converted (step S112: No), the generation unit 12 performs step S114.

Step S113

The generation unit 12 performs processing for converting the periodic graph into a three-dimensional structure. The conversion processing can be, for example, performed by using a method indicated by the Kotani-Sunada theory (Kotani-Sunada, 2000, Trans. Amer. Mat). Next, the generation unit 12 performs step S114.

Step S114

The generation unit 12 determines whether or not there is a periodic graph that has not determined as to whether or not it can be converted. In a case where there is a periodic graph that has not determined (S114: Yes), the generation unit 12 returns to step S112. In a case where all the periodic graphs have been determined (S114: No), the processing of the generation unit 12 is completed. Then, the information processing system 100 (the information processing method) performs step S115.

Step S115

The output unit 13 performs processing for outputting the second information generated by the generation unit 12. In this example, the output unit 13 outputs the second information by causing the second image indicative of the second information generated by the generation unit 12 to be displayed on the display unit 3.

The display unit 3 may include the display control unit 30. The display unit 3 including the display control unit 30 may be referred to as a display unit 3A. The output unit 13 may output the second information generated by the generation unit 12 to the display unit 3A. The display unit 3A may thus display the second information. That is, the output unit 13 may cause the second information to be displayed on the display unit 3A.

Figure 29:
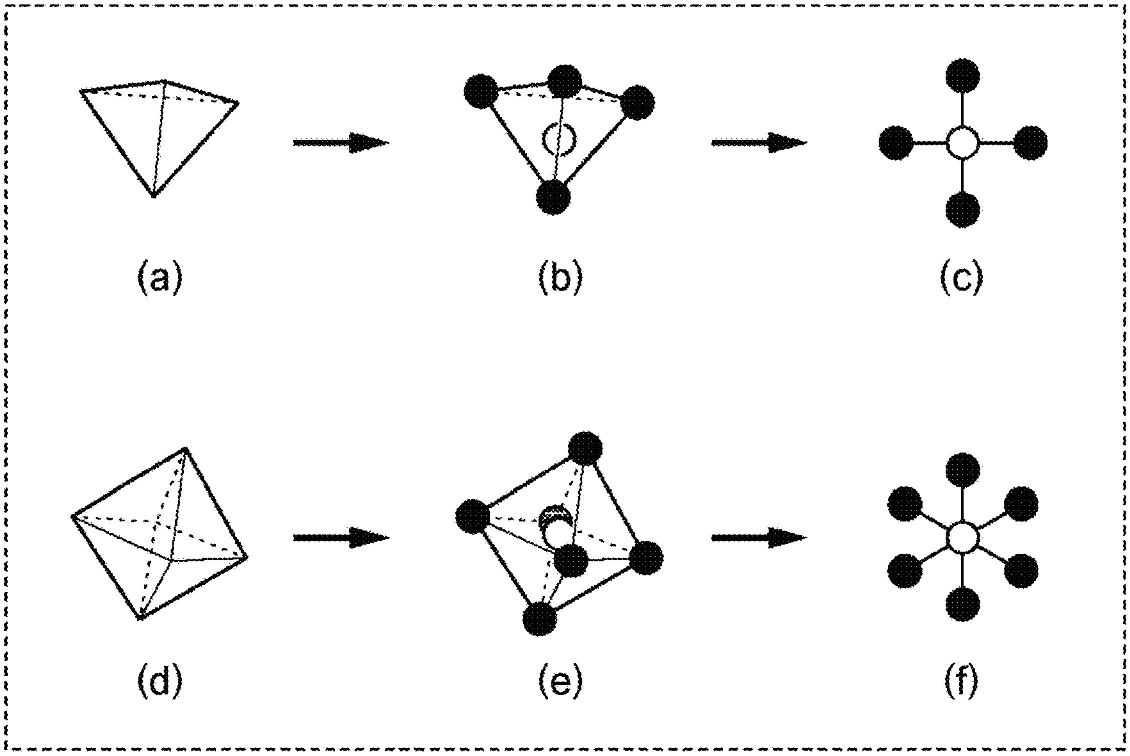
FIG. 29 illustrates a specific example of a process for converting a polyhedron into a polyhedron graph.
Figure 30:
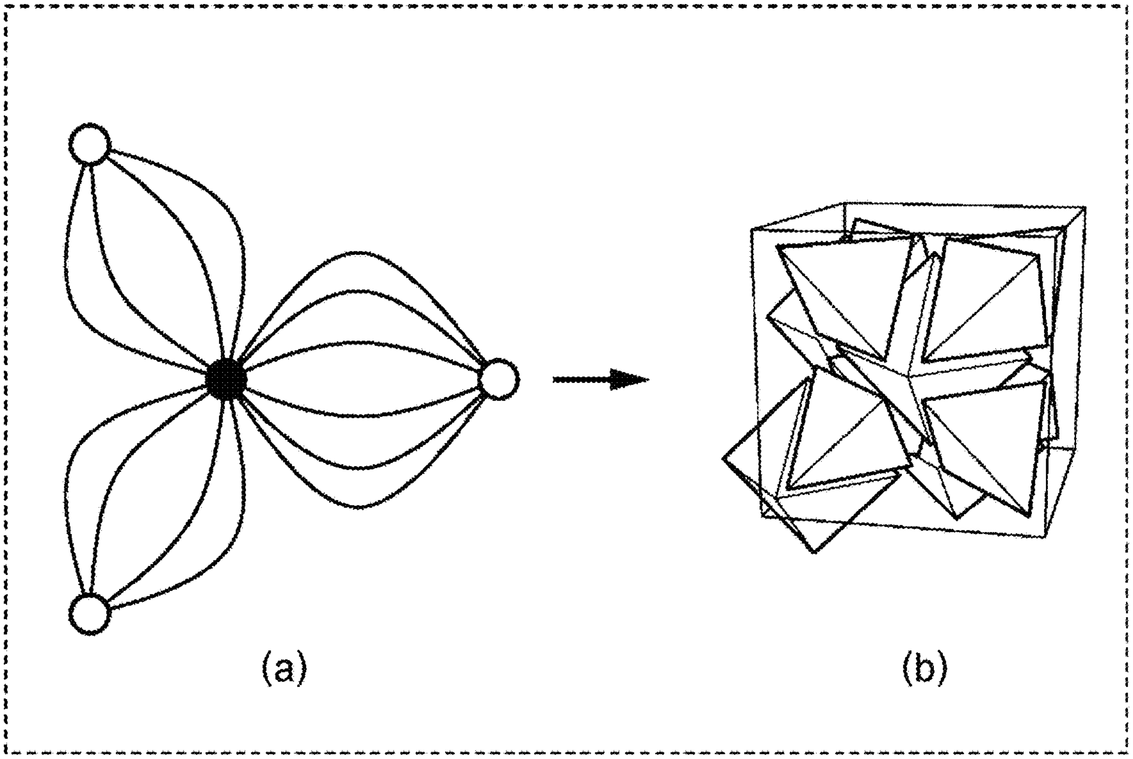
FIG. 30 illustrates a specific example of a case where a periodic graph is converted into a three-dimensional structure.

A specific example of the processing for generating a three-dimensional structure from polyhedra is described below with reference to the drawings. FIG. 29 illustrates a specific example of a process for converting polyhedra into polyhedron graphs. FIG. 30 illustrates a specific example of a case where a periodic graph is converted into a three-dimensional structure.

First, the generation unit 12 determines vertex sites of a polyhedron and a center site of the polyhedron. In the case of a regular tetrahedron illustrated in FIG. 29(*a*), the generation unit 12 determines four vertex sites and one center site as illustrated in FIG. 29(*b*). In the case of a regular octahedron illustrated in FIG. 29(*d*), the generation unit 12 determines six vertex sites and one center site as illustrated in FIG. 29(*e*).

Next, the generation unit 12 generates a polyhedron graph by connecting the vertex sites and the center site of the polyhedron. In the case where the polyhedron is a regular tetrahedron, the generation unit 12 generates a polyhedron graph in which an edge extends from the center node to each of the four vertex nodes, as illustrated in FIG. 29(*c*). In a case where the polyhedron is a regular octahedron, the generation unit 12 generates a polyhedron graph in which an edge extends from the center node to each of the six vertex nodes, as illustrated in FIG. 29(*f*).

Next, the generation unit 12 generates a periodic graph by coupling the vertex nodes of the generated polyhedron graphs. The periodic graph illustrated in FIG. 30(*a*) is a periodic graph generated from two polyhedron graphs corresponding to two regular tetrahedra and one polyhedron graph corresponding to one regular octahedron. This periodic graph is generated by coupling the vertex nodes of the polyhedron graphs into one. Then, the generation unit 12 converts the generated periodic graph into a three-dimensional structure. The three-dimensional structure (fcc-type structure) illustrated in FIG. 30(*b*) is generated by converting the periodic graph illustrated in FIG. 30(*a*).

Embodiment 2

An information processing system 200 (an information processing method, or a recording medium) according to Embodiment 2 of the present disclosure is described in detail below with reference to the drawings. The information processing system 200 according to Embodiment 2 is different from the information processing system 100 according to Embodiment 1 in that an acquisition unit 11 acquires material information concerning a composition of a material as first information. Note that the information processing system 200 according to Embodiment 2 includes the acquisition unit 11, a generation unit 12, and an output unit 13 and has a similar configuration to the information processing system 100 according to Embodiment 1, and therefore description of these constituent elements is omitted.

Use Examples

Use examples of the information processing system 200 according to Embodiment 2 are listed below. In the description of a second use example below, description of points identical to a first use example is omitted.

Figure 31A:
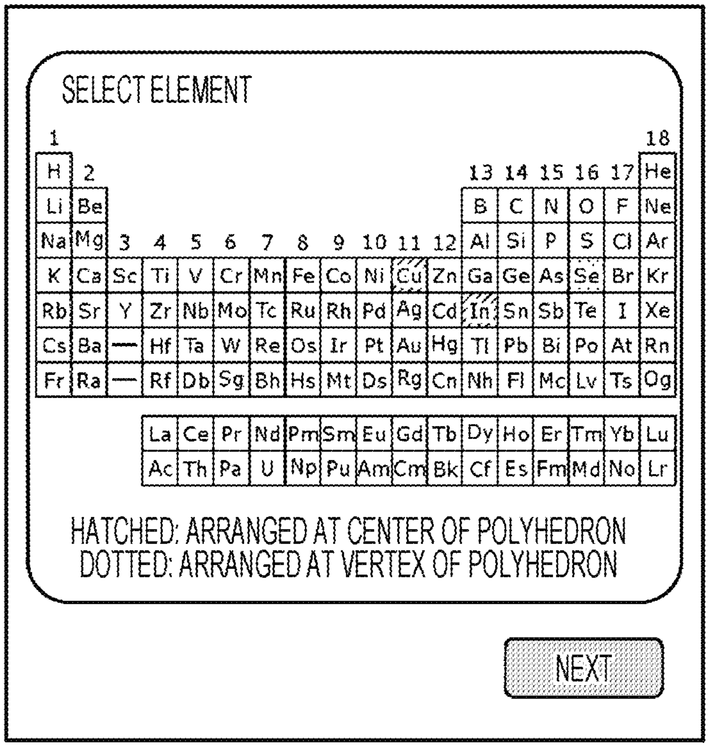
FIGS. 31A and 31B illustrate an image displayed on a display unit in a first use example of Embodiment 2.
Figure 31B:
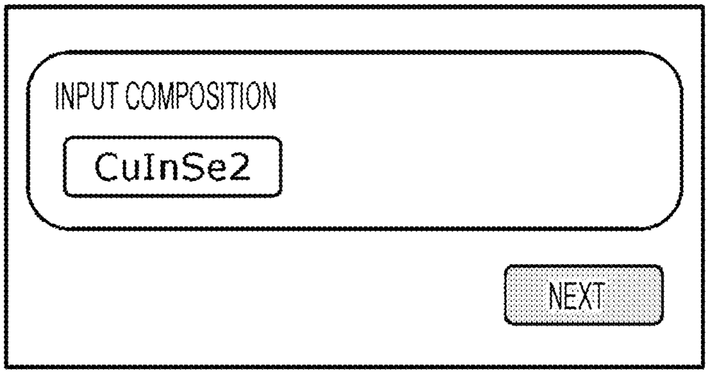

FIGS. 31A and 31B, 32, and 33 each illustrate an image displayed on the display unit 3 in the first use example of Embodiment 2. FIGS. 31A and 31B each illustrate an example of a first image initially displayed on the display unit 3. The display unit 3 may display the first image illustrated in FIG. 31A or may display the first image illustrated in FIG. 31B.

The first image illustrated in FIG. 31A includes an element selection region for selecting an element and an execution icon “NEXT”. In the element selection region, a periodic table is displayed. A user selects an element (atom) contained in a desired material in the element selection region. For example, in a case where the user performs the operation of selecting an element one time, the element becomes an element disposed at a center of a polyhedron. On the other hand, in a case where the user performs the operation of selecting an element two times, the element becomes an element disposed at a vertex of the polyhedron. Then, when the user selects the execution icon, the acquisition unit 11 (in a step of acquiring the first information) acquires, as the first information, material information concerning a composition of a material (in this example, atoms contained in the material.

The first image illustrated in FIG. 31B includes a composition designation region for designating a composition of a material and an execution icon "NEXT". In the composition designation region, a textbox for designating a composition of a material desired by a user is displayed. The user inputs a composition formula of a desired material in the textbox. Then, when the user selects the execution icon, the acquisition unit 11 (in the step of acquiring the first information) acquires, as the first information, material information concerning a composition of a material (in this example, a composition of a material itself). Note that expression using a subscript is omitted in the composition formula illustrated in FIG. 31B.

Figure 32:
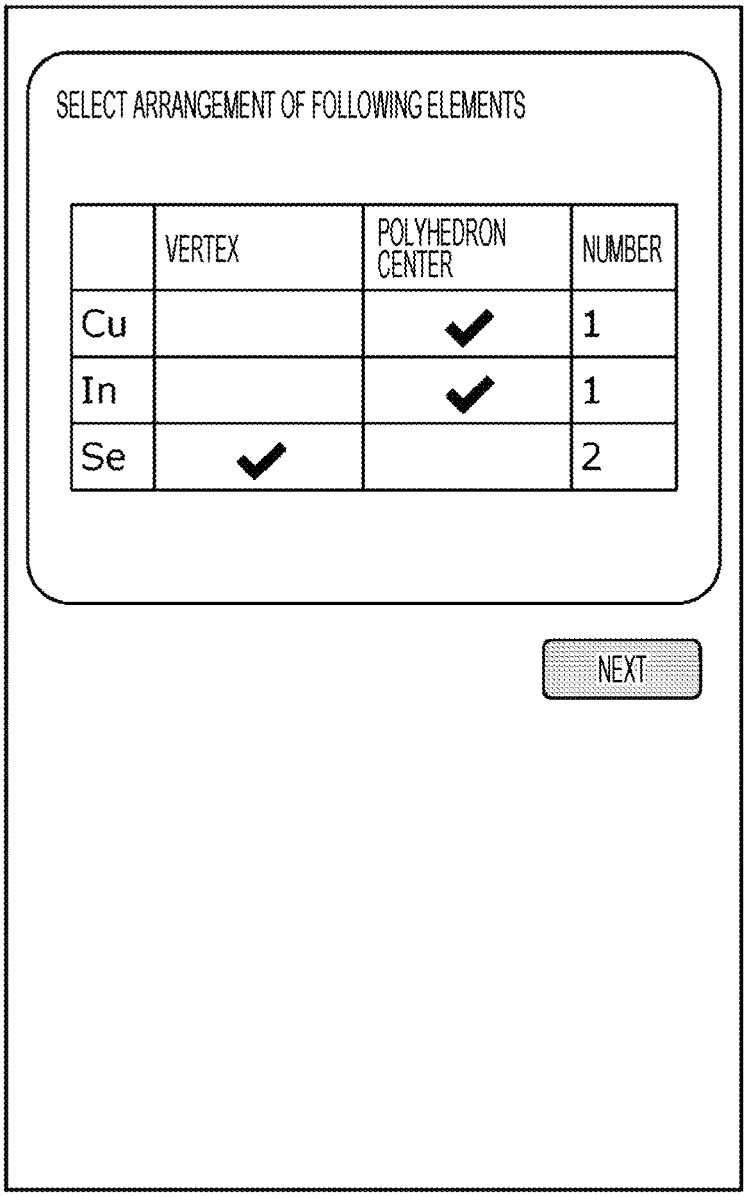
FIG. 32 illustrates an image displayed on the display unit in the first use example of Embodiment 2.

FIG. 32 illustrates an example of a first image displayed next on the display unit 3. The first image illustrated in FIG. 32 is displayed on the display unit 3 in a case where the user selects the execution icon in the first image illustrated in FIG. 31A or the first image illustrated in FIG. 31B. In the first image illustrated in FIG. 32, an arrangement designation region for designating an arrangement of elements (atoms) included in a material and an execution icon "NEXT" are displayed. In the arrangement designation region, a table showing the number of elements of each kind included in a polyhedron and a position (a vertex or a center) of each element in the polyhedron is displayed.

In a case where the first image illustrated in FIG. 32 is displayed on the display unit 3 next to the first image illustrated in FIG. 31A, a position of each element is already designated in the arrangement designation region. Accordingly, the user selects the number of elements of each kind in a polyhedron and selects the execution icon. In this case, the acquisition unit 11 (in the step of acquiring the first information) acquires, as the first information, arrangement information concerning an arrangement of elements (atoms) in a three-dimensional structure.

On the other hand, in a case where the first image illustrated in FIG. 32 is displayed on the display unit 3 next to the first image illustrated in FIG. 31B, the number of elements of each kind is already designated in the arrangement designation region. Accordingly, the user selects an arrangement of elements in a polyhedron and selects the execution icon. Also in this case, the acquisition unit 11 (in the step of acquiring the first information) acquires, as the first information, arrangement information concerning an arrangement of elements (atoms) in a three-dimensional structure.

Figure 33:
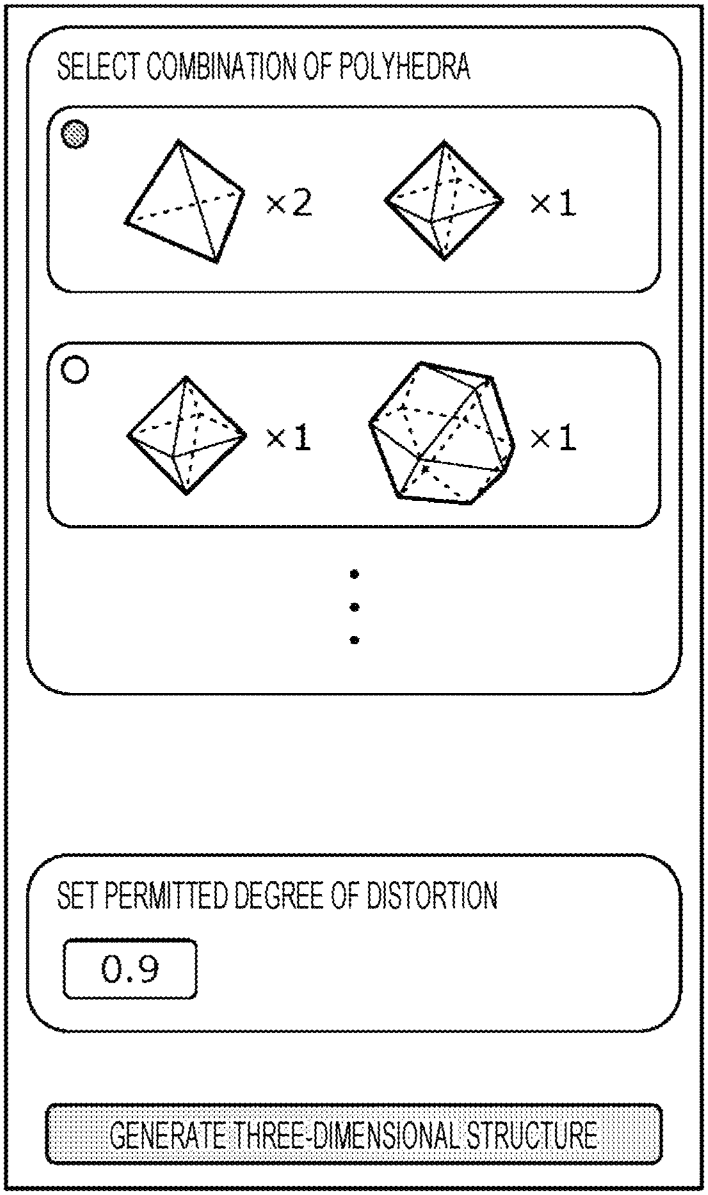
FIG. 33 illustrates an image displayed on the display unit in the first use example of Embodiment 2.

FIG. 33 illustrates an example of a first image displayed next on the display unit 3. The first image illustrated in FIG. 33 is displayed on the display unit 3 in a case where the user selects the execution icon in the first image illustrated in FIG. 32. The first image illustrated in FIG. 33 includes a combination selection region for selecting a combination of polyhedra, a distortion degree designation region, and an execution icon "GENERATE THREE-DIMENSIONAL STRUCTURE". Note that the first image illustrated in FIG. 33 may include, for example, a unit structure selection region instead of the distortion degree designation region. That is, any one of the first to fifth use examples of Embodiment 1 or a combination of these use examples may be applied to the first image illustrated in FIG. 33 except for the combination selection region.

In the combination selection region, combinations of polyhedra based on the arrangement information that can be selected by the user and selection buttons corresponding to the combinations of polyhedra are displayed. Note that names of shapes of polyhedra may be displayed in the combination selection region. In the combination selection region, each polyhedron may be displayed not as a still image, but as a moving image. In the combination selection region, the user selects a combination of polyhedra to be included in a three-dimensional structure. As a result, the acquisition unit 11 (in the step of acquiring the first information) acquires, as the first information, shape information indicative of shapes of the polyhedra and composition ratio information indicative of a composition ratio based on shapes.

Then, when the user selects the execution icon, the following processing is performed.

The generation unit 12 decides number information indicative of the number of polyhedra for each shape on the basis of the composition ratio information. The number information may be pieces of number information. For example, assume that information indicating the number of regular tetrahedrons: the number of regular octahedrons=2:1 is selected in FIG. 33. The pieces of number information may be information indicating that (the number of regular tetrahedrons is 2, the number of regular octahedrons is 1), (the number of regular tetrahedrons is 4, the number of regular octahedrons is 2), . . . , and (the number of regular tetrahedrons is 2×n, the number of regular octahedrons is 1×n). n may be a predetermined value that is a natural number of 2 or more. The following processing may be performed on each of the pieces of number information.

The generation unit 12 (in a step of generating the second information) generates second information concerning a three-dimensional structure in which polyhedra of shapes indicated by the shape information are arranged without any gaps so that the number of polyhedral of each shape becomes a corresponding number. In other words, the generation unit 12 generates second information concerning a three-dimensional structure in which polyhedra of shapes indicated by the shape information are arranged without any gaps at a composition ratio based on the shape indicated by the composition ratio information. The shape information and the composition ratio information are information based on the arrangement information. It can therefore be said that the generation unit 12 (in the step of generating the second information) generates second information concerning a three-dimensional structure on the basis of an arrangement of elements (atoms) indicated by the arrangement information.

Then, the second image is displayed on the display unit 3, as in the first use example of Embodiment 1. When the user selects a three-dimensional structure to be saved and a saving format of the three-dimensional structure, second information concerning the three-dimensional structure selected by the user is saved in the second storage unit 5.

Figure 34:
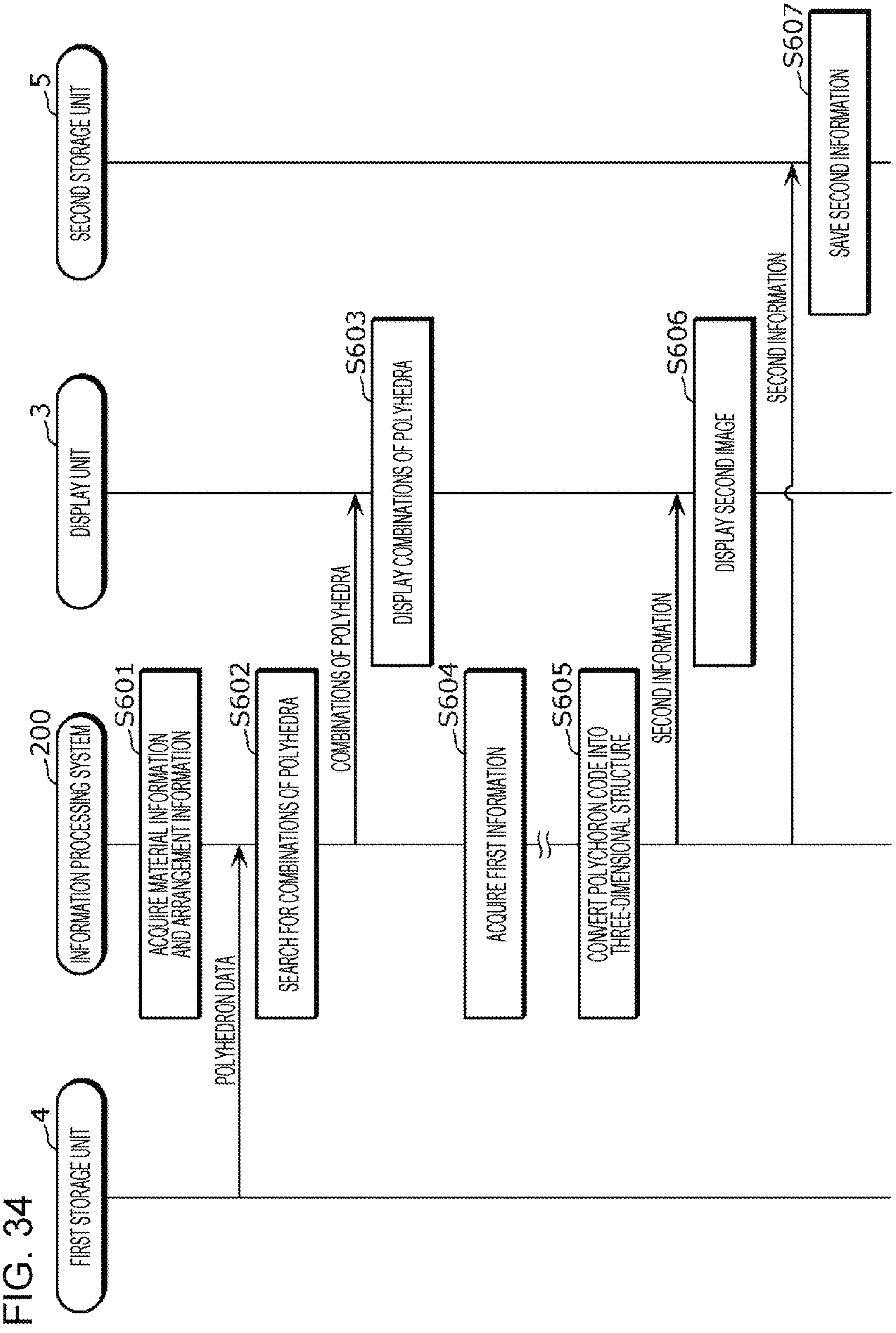
FIG. 34 is a sequence diagram illustrating a first operation example of an information processing system and the display unit, a first storage unit, and a second storage unit according to Embodiment 2.

A first operation example of the information processing system 200 and the display unit 3, the first storage unit 4, and the second storage unit 5 according to Embodiment 2 is described below with reference to the drawings. FIG. 34 is a sequence diagram illustrating a first operation example of the information processing system 200 and the display unit 3, the first storage unit 4, and the second storage unit 5 according to Embodiment 2.

Step S601

The acquisition unit 11 of the information processing system 200 acquires material information and arrangement information. In this example, a user inputs (selects) the material information while seeing the first image (see FIGS. 31A and 31B) initially displayed on the display unit 3. In this way, the material information is acquired by the acquisition unit 11. Furthermore, the user inputs (selects) the arrangement information while seeing the first image (see FIG. 32) displayed next on the display unit 3. In this way, the arrangement information is acquired by the acquisition unit 11.

Step S602

The acquisition unit 11 of the information processing system 200 searches for combinations of polyhedra based on the arrangement information that can be selected by the user. When searching for the combinations of polyhedra, the acquisition unit 11 reads out and refers to polyhedron data stored in the first storage unit 4.

Step S603

The display unit 3 displays the combinations of polyhedra output from the output unit 13 of the information processing system 200. In other words, the display unit 3 displays a first image including the combination selection region for selecting a combination of polyhedra.

Step S604

The acquisition unit 11 of the information processing system 200 acquires the first information. In this example, the first information is shape information and composition ratio information, and the user inputs (selects) the first information by using the input unit 2 while seeing the first image (see FIG. 33) displayed next on the display unit 3. In this way, the first information is acquired by the acquisition unit 11.

Step S605

The generation unit 12 of the information processing system 200 performs processing for converting a polychoron code determined as being convertible into a three-dimensional structure. Note that step S605 is processing identical to step S505 (see FIG. 27). Between step S604 and step S605, processing identical to step S502 to step S504 (see FIG. 27) is performed.

Step S606

The display unit 3 displays a second image indicative of the second information output from the output unit 13 of the information processing system 200.

Step S607

When the user selects a three-dimensional structure to be saved while seeing the second image displayed on the display unit 3, the information processing system 200 gives second information concerning the selected three-dimensional structure to the second storage unit 5. As a result, the second storage unit 5 stores therein the second information concerning the three-dimensional structure selected by the user.

Figure 35:
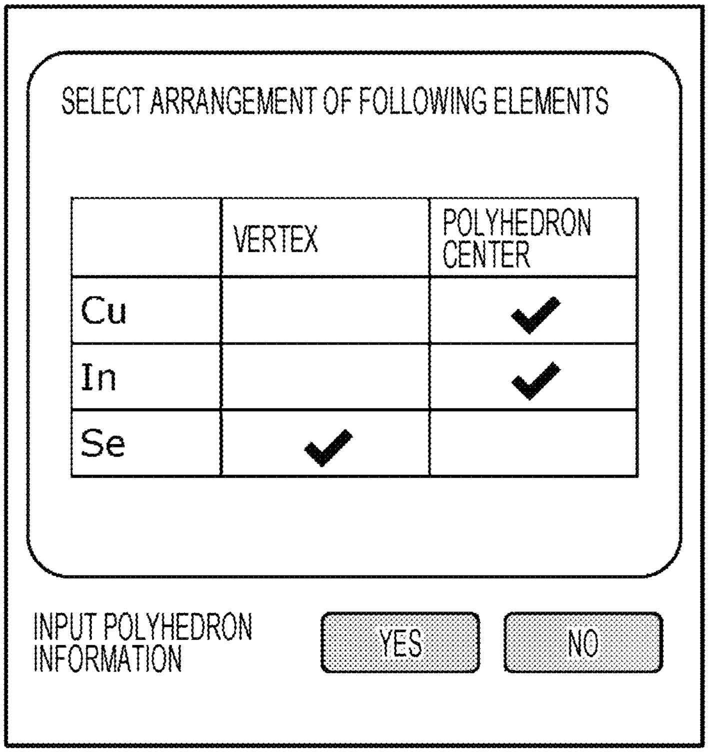
FIG. 35 illustrates an image displayed on the display unit in a second use example of Embodiment 2.
Figure 36:
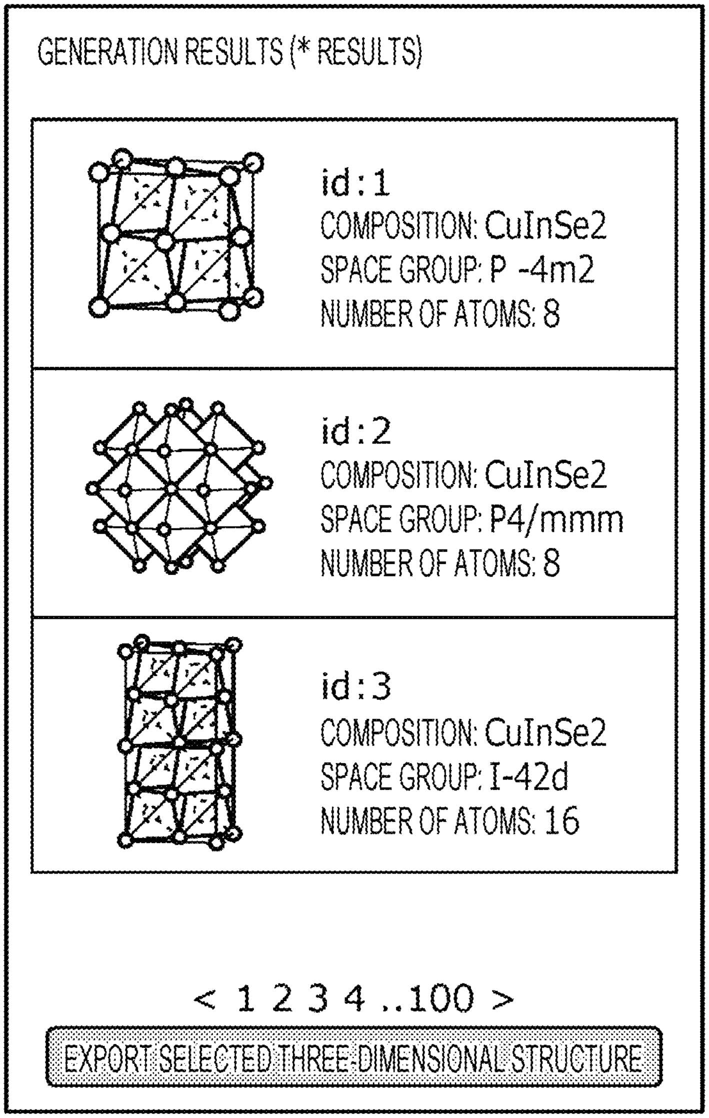
FIG. 36 illustrates an image displayed on the display unit in the second use example of Embodiment 2.

FIGS. 35 and 36 each illustrate an image displayed on the display unit 3 in the second use example of Embodiment 2. FIG. 35 illustrates an example of the first image displayed next to the initial image on the display unit 3. In the second use example, the first image illustrated in FIG. 35 is displayed on the display unit 3 instead of the first image illustrated in FIG. 32. The first image illustrated in FIG. 35 includes a first execution icon "YES" for inputting polyhedron information and a second execution icon "NO" for omitting input of polyhedron information instead of the execution icon "NEXT", unlike the first image illustrated in FIG. 32.

In a case where the user selects the first execution icon in the first image illustrated in FIG. 35, a first image (see FIG. 8A, FIG. 11, FIG. 13, FIG. 14, and FIG. 15A) prompting input of polyhedron information, for example, any one of the first to fifth use examples of Embodiment 1 or a combination of these use examples is displayed on the display unit 3. Therefore, when the user inputs (selects) polyhedron information while seeing the first image displayed on the display unit 3, the acquisition unit 11 (in the step of acquiring the first information) acquires the polyhedron information (first information). Then, when the user selects the execution icon, the generation unit 12 (in the step of generating the second information) generates second information concerning a crystal structure which a composition of a material can take as a three-dimensional structure. In this case, the generation unit 12 generates the second information on the basis of not only the material information and arrangement information, but also the polyhedron information.

On the other hand, also in a case where the user selects the second execution icon in the first image illustrated in FIG. 35, the generation unit 12 (in the step of generating the second information) generates second information concerning a crystal structure which a composition of a material can take as a three-dimensional structure. In this case, the generation unit 12 generates the second information on the basis of the material information and arrangement information.

FIG. 36 illustrates an example of the second image displayed on the display unit 3. The second image is displayed on the display unit 3 after the generation unit 12 generates second information concerning a three-dimensional structure (in this example, a crystal structure). The second image includes a list of crystal structures generated by the generation unit 12 and an execution icon "EXPORT SELECTED CRYSTAL STRUCTURE".

The user selects a crystal structure to be saved and selects the execution icon. Then, when the user selects a desired saving format, second information concerning the crystal structure selected by the user is saved in the second storage unit 5, as in Embodiment 1.

Figure 37:
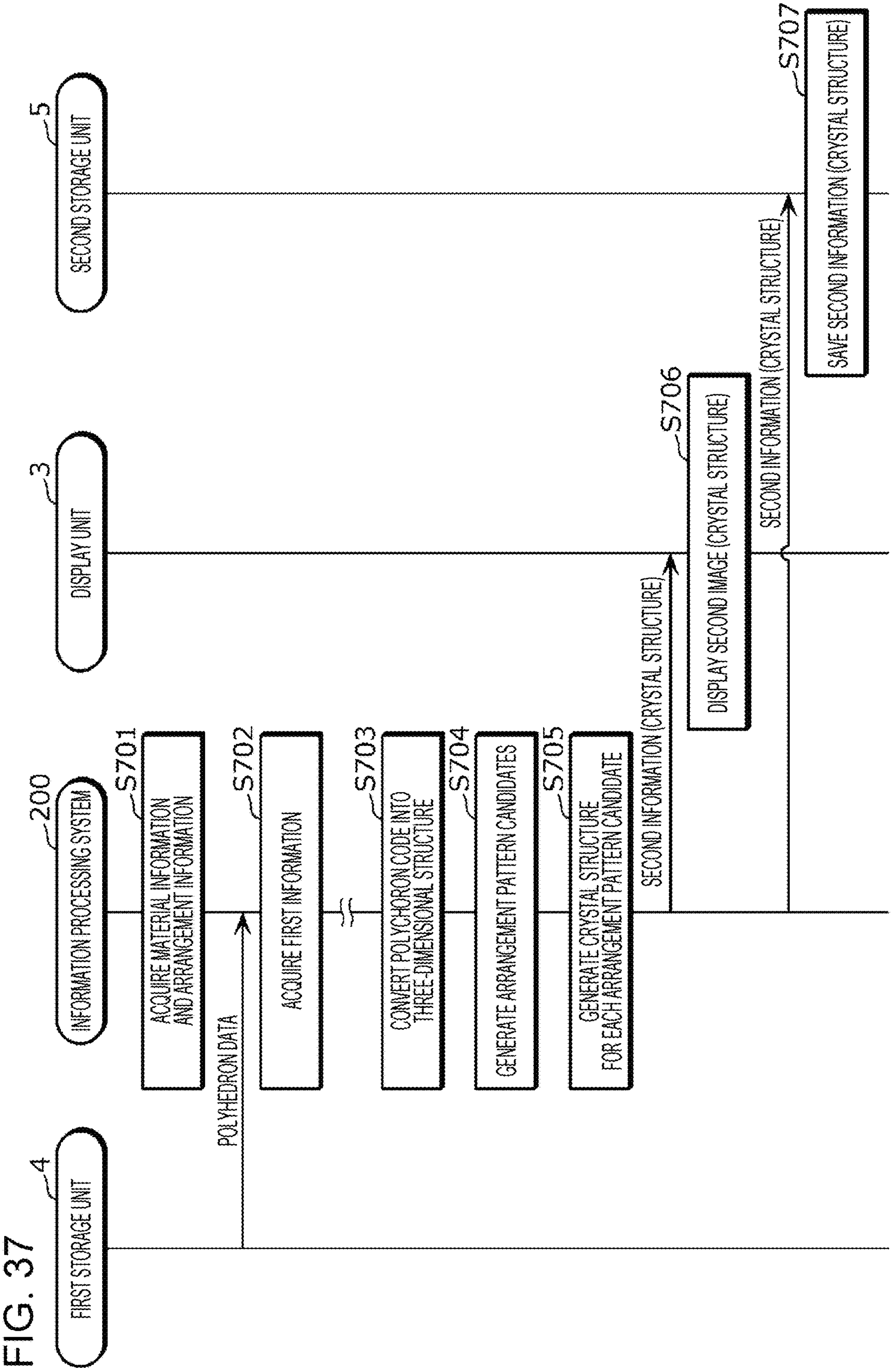
FIG. 37 is a sequence diagram illustrating a second operation example of the information processing system and the display unit, the first storage unit, and the second storage unit according to Embodiment 2.

A second operation example of the whole including the information processing system 200 according to Embodiment 2 is described below with reference to the drawings. FIG. 37 is a sequence diagram illustrating a second operation example of the information processing system 200, the display unit 3, the first storage unit 4, and the second storage unit 5 according to Embodiment 2. It is assumed here that the user inputs polyhedron information.

Step S701

The acquisition unit 11 of the information processing system 200 acquires material information and arrangement information. In this example, the user inputs (selects) the material information by using the input unit 2 while seeing the first image (see FIGS. 31A and 31B) initially displayed on the display unit 3. In this way, the material information is acquired by the acquisition unit 11. The ser inputs (selects) the arrangement information by using the input unit 2 while seeing the first image (see FIG. 32) displayed next to the initial first image on the display unit 3. In this way, the arrangement information is acquired by the acquisition unit 11.

Step S702

The acquisition unit 11 of the information processing system 200 acquires the first information. In this example, the first information is polyhedron information, and the user inputs (selects) the first information by using the input unit 2 while seeing the first image displayed on the display unit 3. In this way, the first information is acquired by the acquisition unit 11.

Step S703

The generation unit 12 of the information processing system 200 performs processing for converting a polychoron code determined as being convertible into a three-dimensional structure. Note that step S703 is processing identical to step S505 (see FIG. 27). Between step S702 and step S703, processing identical to step S502 to step S504 (see FIG. 27) is performed.

Step S704

The generation unit 12 of the information processing system 200 generates arrangement pattern candidates for each generated three-dimensional structure. The arrangement pattern candidates are candidates of patterns of elements (atoms) arranged at vertexes and a center of each polyhedron included in the three-dimensional structure. Note that the arrangement pattern candidates can include a pattern in which no element is arranged at a center of a polyhedron.

Step S705

The generation unit 12 of the information processing system 200 generates a crystal structure for each arrangement pattern candidate. Specifically, the generation unit 12 generates a crystal structure by arranging an element (atom) at vertexes and a center of each polyhedron in accordance with the arrangement pattern candidate.

Step S706

The display unit 3 displays a second image indicative of second information concerning the crystal structure output from the output unit 13 of the information processing system 200.

Step S707

When the user selects a crystal structure to be saved while seeing the second image displayed on the display unit 3, the information processing system 200 gives second information concerning the selected crystal structure to the second storage unit 5. In this way, the second storage unit 5 stores therein the second information concerning the crystal structure selected by the user.

As described above, in Embodiment 2, by inputting material information concerning a composition of a material, a three-dimensional structure (i.e., a space-filled structure in a three-dimensional space) combining polyhedra based on the input material information can be exhaustively generated. Therefore, in Embodiment 2, a three-dimensional structure concerning a material which a user wants to search for can be generated.

Modifications

Although an information processing system (information processing method) according to one or more aspects of the present disclosure has been described above on the basis of the embodiments, the present disclosure is not limited to these embodiments. Various modifications of the above embodiments which a person skilled in the art can think of may be encompassed within the present disclosure without departing from the spirit of the present disclosure. Furthermore, combinations of constituent elements in different embodiments may also be encompassed within the present disclosure.

For example, although the second information is information indicative of a three-dimensional structure itself in the above embodiments, this is not restrictive. For example, the second information may include at least one of information indicative of a three-dimensional structure, information indicative of a numerical sequence (e.g., a polychoron code) representing a three-dimensional structure, or information indicative of a periodic graph representing a three-dimensional structure.

For example, although the information processing systems 100 and 200 display the first image or the second image on the display unit 3 in the above embodiments, this is not restrictive. For example, the information processing systems 100 and 200 may output information included in the first image or the second image instead of displaying the first image or the second image itself on the display unit 3.

Although the acquisition unit 11 of each of the information processing systems 100 and 200 acquires the first information input by the user by using the input unit 2 in the above embodiments, this is not restrictive. For example, the acquisition unit 11 may acquire the first information by reading out information stored in the first storage unit 4 without receiving user's input.

Although the first storage unit 4 and the second storage unit 5 are realized by different recording media in the above embodiments, this is not restrictive. For example, the first storage unit 4 and the second storage unit 5 may be realized by the same recording medium.

Although each of the information processing systems 100 and 200 includes the acquisition unit 11, the generation unit 12, and the output unit 13 in the above embodiments, this is not restrictive. For example, the information processing system 100 may include the display control unit 30 and the display unit 3, as indicated by "100A" in FIG. 5. Similarly, the information processing system 200 may include the display control unit 30 and the display unit 3.

Note that in the above embodiments, each constituent element may be realized by dedicated hardware or may be realized by execution of a software program suitable for the constituent element. Each constituent element may be realized by reading out and executing a software program recorded in a recording medium such as a hard disk or a semiconductor memory by a program execution unit such as a central processing unit (CPU) or a processor.

Note that the following cases are also encompassed within the present disclosure.

(1) At least one of the apparatuses described above is specifically a computer system that includes a microprocessor, a Read Only Memory (ROM), a Random Access Memory (RAM), a hard disk unit, a display unit, a keyboard, a mouse, and the like. A computer program is stored in the RAM or the hard disk unit. The microprocessor operates in accordance with the computer program, and thus the at least one of the apparatuses accomplishes a function thereof. The computer program is a combination of command codes indicating a command given to a computer for accomplishment of a predetermined function.

(2) Part of or all of constituent elements that constitute at least one of the apparatuses may include a single system large scale integration (LSI). The system LSI is a super-multi-function LSI produced by integrating constituents on a single chip and is specifically a computer system including a microprocessor, a ROM, a RAM, and the like. A computer program is stored in the RAM. The microprocessor operates in accordance with the computer program, and thus the system LSI accomplishes a function thereof.

(3) Part of or all of constituent elements that constitute at least one of the apparatuses may include an IC card that can be detachably attached to the apparatus or a stand-alone module. The IC card or the module is a computer system that includes a microprocessor, a ROM, a RAM, and the like. The IC card or the module may include the super-multi-function LSI. The microprocessor operates in accordance with a computer program, and thus the IC card or the module accomplishes a function thereof. The IC card or the module may have tamper resistance.

(4) The present disclosure may be the methods described above. The present disclosure may be a computer program for causing a computer to realize these methods or may be a digital signal represented by the computer program.

(5) The present disclosure may be a computer-readable recording medium, such as a flexible disc, a hard disk, a Compact Disc (CD)-ROM, a DVD, a DVD-ROM, a DVD-RAM, a Blu-ray (Registered Trademark) (BD) Disc, or a semiconductor memory, on which the computer program or the digital signal is recorded. The present disclosure may be the digital signal recorded on such a recording medium.

(6) The present disclosure may be the computer program or the digital signal transmitted over an electric communication line, a wireless or wired communication line, a network represented by the Internet, data broadcasting, or the like.

The program or the digital signal may be executed by another independent computer system by transporting the program or the digital signal on the recording medium or transporting the program or the digital signal over the network or the like.

OTHER REMARKS

A modification of the embodiments of the present disclosure may be as follows.

A method being performed by one or more processors configured to execute instructions stored in one or more memories, the method including:

receiving shape information including first information on a shape of a first polyhedron, . . . , and n-th information on a shape of an n-th polyhedron, n being an integer of 1 or more;

receiving number information including a first number corresponding to the first polyhedron, . . . , and an n-th number corresponding to the n-th polyhedron, so that one or more first polyhedra corresponding to the first polyhedron and the first number, . . . , and one or more n-th polyhedra corresponding to the n-th polyhedron and the n-th number are decided;

rearranging codes including one or more first codes, . . . , and one or more n-th codes, so that polychoron codes are decided (see, for example, FIG. 23), the one or more first codes corresponding to first codes for the first number and the first polyhedron . . . , and the one or more n-th codes corresponding to n-th codes for the n-th number and the n-th polyhedron, the first codes being decided on the basis of the number of sides of each of faces included in the first polyhedron, . . . , and the n-th code being decided on the basis of the number of sides of each of faces included in the n-th polyhedron (see, for example, FIGS. 20, 21, and 22);

deciding a three-dimensional structure including the one or more first polyhedra, . . . , and the one or more n-th polyhedra on the basis of the polychoron codes (see, for example, FIG. 24);

generating an image of the three-dimensional structure and second information including three-dimensional coordinates included in the three-dimensional structure; and outputting the image and the second information, in which the three-dimensional structure does not include one or more polyhedra other than the one or more first polyhedra, . . . , and the one or more n-th polyhedra, any two polyhedra selected from among the one or more first polyhedra, . . . , and the one or more n-th polyhedra do not overlap each other, and positions included in the three-dimensional structure correspond to positions of atoms included in a crystal structure.

The present disclosure is useful for searching for an unknown material.

What is claimed is:

1. An information processing method including a computer executing the information processing method, comprising:

acquiring first information concerning polyhedra;

generating second information concerning a three-dimensional structure in which the polyhedra are arranged on a basis of the first information; and outputting the second information thus generated, wherein the three-dimensional structure is a structure in which the polyhedra are arranged without any gaps and becomes a crystal structure in a case where atoms are arranged, in the acquiring the first information, shape information indicative of shapes of the polyhedra is acquired as the first information, in the generating the second information, the second information concerning the three-dimensional structure in which the polyhedra having the shapes indicated by the shape information are arranged without any gaps is generated, in the acquiring the first information, distortion degree information indicative of a permitted degree of distortion of the shapes of the polyhedra is further acquired as the first information, and in the generating the second information, the second information concerning the three-dimensional structure in which at least one of the polyhedra is distorted so that the distortion does not exceed the degree of distortion indicated by the distortion degree information is generated.

2. The information processing method according to claim 1, wherein the second information includes at least one of information indicative of the three-dimensional structure, information indicative of a numerical sequence including a numeral or a character representing the three-dimensional structure, or information indicative of a periodic graph representing the three-dimensional structure.

3. The information processing method according to claim 1, wherein in the acquiring the first information, unit structure information indicative of a shape of a unit structure in which the polyhedra are arranged without any gaps is acquired as the first information, and in the generating the second information, the second information concerning the three-dimensional structure in which at least one unit structure indicated by the unit structure information is arranged is generated.

4. The information processing method according to claim 3, wherein the unit structure information is information indicative of a Bravais lattice in the crystal structure.

5. The information processing method according to claim 1, wherein in the acquiring the first information, symmetry information indicative of symmetry of the three-dimensional structure is acquired as the first information, and in the generating the second information, the second information concerning the three-dimensional structure having the symmetry indicated by the symmetry information is generated.

6. The information processing method according to claim 5, wherein the symmetry information is information indicative of a space group in the crystal structure.

7. The information processing method according to claim 1, wherein in the acquiring the first information, number information indicative of the number of polyhedra for each shape is further acquired as the first information, and in the generating the second information, the second information concerning the three-dimensional structure in which the polyhedra having the shapes indicated by the shape information are arranged without any gaps so that the number of polyhedral of each shape becomes the number indicated by the number information is generated.

8. The information processing method according to claim 1, wherein in the acquiring the first information, composition ratio information indicative of a composition ratio of the polyhedra based on the shapes is further acquired as the first information, and in the generating the second information, the second information concerning the three-dimensional structure in which the polyhedra having the shapes indicated by the shape information are arranged without any gaps at the composition ratio based on the shapes indicated by the composition ratio information is generated.

9. The information processing method according to claim 1, wherein the degree of distortion is decided on a basis of at least one of a position of a center of gravity of the polyhedron, a position of at least one vertex of the polyhedron, a length of at least one side of the polyhedron, an angle formed by at least two sides of the polyhedron, or an area of at least one face of the polyhedron while using a shape of the polyhedron indicated by the shape information as a reference.

10. The information processing method according to claim 1, wherein the generating the second information includes converting the acquired first information into first numerical sequences representing the polyhedra and converting a second numerical sequence representing a polychoron generated by using the first numerical sequences thus obtained into the three-dimensional structure.

11. The information processing method according to claim 1, wherein the generating the second information includes converting the acquired first information into polyhedron graphs representing the polyhedra and converting a periodic graph generated by using the polyhedron graphs thus obtained into the three-dimensional structure.

12. The information processing method according to claim 1, wherein in the acquiring the first information, material information concerning a composition of a material is acquired as the first information.

13. The information processing method according to claim 12, wherein the material information includes at least one of an atom contained in the material or the composition of the material, in the acquiring the first information, arrangement information concerning an arrangement of the atom in the three-dimensional structure is further acquired as the first information, and in the generating the second information, the second information concerning the three-dimensional structure is generated on a basis of the arrangement of the atom indicated by the arrangement information.

14. The information processing method according to claim 12, wherein the three-dimensional structure generated in the generating the second information is the crystal structure which the composition of the material can take.

15. An information processing system comprising:

a display controller, wherein after a first image for receiving first information concerning polyhedra is displayed on a display, the display controller causes a second image showing second information concerning a three-dimensional structure in which the polyhedra are arranged to be displayed on the display, the second information being generated on a basis of the input first information, and the three-dimensional structure is a structure in which the polyhedra are arranged without any gaps and becomes a crystal structure in a case where atoms are arranged, shape information indicative of shapes of the polyhedra is received as the first information, the second information is generated on the basis of the first input information such that the second information concerning the three-dimensional structure in which the polyhedra having the shapes indicated by the shape information are arranged without any gaps is generated, distortion degree information indicative of a permitted degree of distortion of the shapes of the polyhedra is further received as the first information, and the second information is generated on the basis of the first input information such that the second information concerning the three-dimensional structure in which at least one of the polyhedra is distorted so that the distortion does not exceed the degree of distortion indicated by the distortion degree information is generated.

16. A non-transitory computer-readable recording medium comprising: a program stored on a computer for performing processing comprising:

acquiring first information concerning polyhedra;

generating second information concerning a three-dimensional structure in which the polyhedra are arranged on a basis of the first information; and outputting the second information thus generated, wherein the three-dimensional structure is a structure in which the polyhedra are arranged without any gaps and becomes a crystal structure in a case where atoms are arranged, in the acquiring the first information, shape information indicative of shapes of the polyhedra is acquired as the first information, in the generating the second information, the second information concerning the three-dimensional structure in which the polyhedra having the shapes indicated by the shape information are arranged without any gaps is generated, in the acquiring the first information, distortion degree information indicative of a permitted degree of distortion of the shapes of the polyhedra is further acquired as the first information, and in the generating the second information, the second information concerning the three-dimensional structure in which at least one of the polyhedra is distorted so that the distortion does not exceed the degree of distortion indicated by the distortion degree information is generated.

* * * * *